(12) United States Patent
Chen et al.

(10) Patent No.: US 11,919,898 B2
(45) Date of Patent: Mar. 5, 2024

(54) CRYSTAL FORM OF AZAINDOLE DERIVATIVE AND USE THEREOF

(71) Applicant: Wuxi Life Fountain Biotech Co., Ltd, Wuxi (CN)

(72) Inventors: Zhengxia Chen, Shanghai (CN); Meibi Dai, Shanghai (CN); Yang Zhang, Shanghai (CN)

(73) Assignee: SHENZHEN LINGFANG BIOTECH CO., LTD., Guangdong (CN)

( * ) Notice: Subject to any disclaimer, the term of this patent is extended or adjusted under 35 U.S.C. 154(b) by 0 days.

(21) Appl. No.: 17/793,350

(22) PCT Filed: Jan. 15, 2021

(86) PCT No.: PCT/CN2021/072247
§ 371 (c)(1),
(2) Date: Feb. 24, 2023

(87) PCT Pub. No.: WO2021/143875
PCT Pub. Date: Jul. 22, 2021

(65) Prior Publication Data
US 2023/0322760 A1    Oct. 12, 2023

(30) Foreign Application Priority Data

Jan. 15, 2020   (CN) .......................... 202010042713.X

(51) Int. Cl.
*C07D 471/04*    (2006.01)
*A61P 35/00*    (2006.01)

(52) U.S. Cl.
CPC ............ *C07D 471/04* (2013.01); *A61P 35/00* (2018.01); *C07B 2200/13* (2013.01)

(58) Field of Classification Search
CPC .................................................... C07D 471/04
USPC ........................................................ 514/300
See application file for complete search history.

(56) References Cited

FOREIGN PATENT DOCUMENTS

| CN | 101641351 A | 2/2010 |
| CN | 104710417 A | 6/2015 |
| WO | 2008124850 A1 | 10/2008 |
| WO | 2010059771 A1 | 5/2010 |
| WO | 2020015744 | * 1/2020 |
| WO | 2020015744 A1 | 1/2020 |

* cited by examiner

*Primary Examiner* — Niloofar Rahmani
(74) *Attorney, Agent, or Firm* — Global IP Services; Tianhua Gu

(57) ABSTRACT

A crystal form of an azaindole derivative and a preparation method thereof are disclosed.

18 Claims, 13 Drawing Sheets

CRYSTAL FORM OF AZAINDOLE DERIVATIVE AND USE THEREOF

CROSS REFERENCE TO RELATED PATENT APPLICATION

The present application is the US national stage of PCT/CN2021/072247 filed on 2021 Jan. 15, which claims the priority of the Chinese patent application No. 202010042713.X filed on 2020 Jan. 15, which application is incorporated herein by reference.

FIELD OF TECHNOLOGY

The present invention relates to a crystal form of an azaindole derivative and a preparation method thereof.

BACKGROUND

Fibroblast growth factor receptors (FGFRs) are a class of biologically active substances having functions such as transducing biological signals, regulating cell growth, and participating in tissue repair. In recent years, several members of the FGFR family are found to play an important role in tumor formation and development. FGFRs are a class of receptor proteins that can specifically bind to fibroblast growth factors (FGFs). The FGFR family includes FGFR1b, FGFR1c, FGFR2b, FGFR2c, FGFR3b, FGFR3c, and FGFR4. Different subtypes of FGFRs bind to different FGFs. The binding of FGFs to FGFRs leads to the auto-phosphorylation of multiple tyrosine residues in the cells. The phosphorylated FGFRs activate downstream signaling pathways including MEK/MAPK, PLCγ/PKC, PI3K/AKT, and STATS, etc. In tumors, such as liver cancer, bladder cancer, lung cancer, breast cancer, endometrial cancer, glioma, prostate cancer, and so on, the activating mutations of FGFRs or ligand/receptor overexpression causes persistent constitutive activation, which is closely related to the occurrence, development, and poor prognosis of tumors, and also plays an important role in tumor angiogenesis, tumor invasion and metastasis. Therefore, FGFRs are considered to be an important therapeutic target of tumors.

c-Met protein (also known as hepatocyte growth factor (HGF) receptor) is a 190-kDa transmembrane heterodimer with tyrosine kinase activity, encoded by the c-Met oncogene. c-MET is the only known receptor of HGF, and the binding of HGF to c-MET can activate the downstream signaling cascades, to phosphorylate the cytoplasmic tyrosine kinase and then cause the autophosphorylation of MET. Various cytoplasmic effector proteins, including GRB2, GAB1, PLC and SOS, are recruited and phosphorylated. Once activated, GAB1 forms a binding site for downstream proteins (PI3K, etc.). It enters the nucleus through the RAS-MAPK and PI3K-AKT signaling pathways and thus affects the gene expression and cell cycle progression. It has been shown that the HGF/c-Met signaling pathway exhibits various cellular responses, including mitogenic activity, proliferative activity, morphogenic activity, and angiogenic activity. c-Met protein is abnormal in about 5-10% of patients with tumors, including patients of liver cancer, gastric cancer, non-small cell lung cancer, bladder cancer, breast cancer, colorectal cancer, head and neck squamous cell carcinoma, hypopharyngeal cancer, ovarian cancer, and others. Inhibitors of the HGF/c-Met pathway are clinically confirmed to have significant potential in the treatment of cancers. The Patent WO 2010059771 reports a small molecule inhibitor with activities against c-Met.

FGFR and c-Met are both members of the receptor tyrosine kinase (RTK) family, and the signaling pathways PI3K-AKT-mTOR and RAS-RAF-MEK-ERK are regulated by the two together. Numerous studies have demonstrated that tumor escape occurs between the FGFR and c-Met targets.

In terms of the molecular mechanism of action, FGFR and FGFR are both members of the receptor tyrosine kinase (RTK) family, and the signaling pathways PI3K-AKT-mTOR and RAS-RAF-MEK-ERK are regulated by the two together. The FGFR and c-Met targets are synergistic and complementary, and the FGFR mutation and c-Met mutation tend to have a signal compensation effect when the other is inhibited, thus making the tumor cells resistant to a single inhibitor.

The Patent WO2010059771A1 discloses Met and RON inhibitors as described in Comparative Examples 1a and 1b. At present, no dual small molecule inhibitor with high activity against both FGFR and c-Met is found.

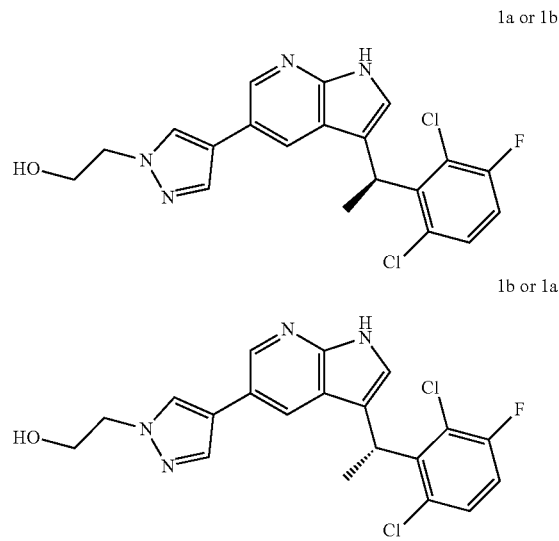

1a or 1b 1b or 1a

SUMMARY

The present invention provides a compound of Formula (II):

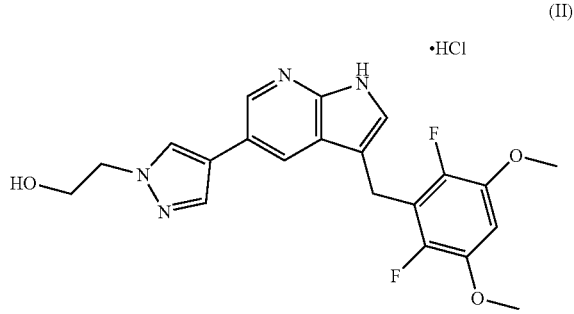 [SMILES: Cl ; COc1cc(OC)c(F)c(Cc2c[nH]c3ncc(-c4cnn(CCO)c4)cc23)c1F]

(II)

The present invention further provides a crystal form A of the compound of Formula (II), having an X-ray powder diffraction (XRPD) pattern with characteristic diffraction peaks at 2θ of 5.40°±0.20°, 11.99°±0.20°, and 14.77°±0.20°.

In some embodiments of the present invention, the crystal form A has an XRPD pattern with characteristic diffraction peaks at 2θ of 5.40±0.20°, 10.77±0.20°, 11.99±0.20°, 14.77±0.20°, 21.55±0.20°, 23.25±0.20°, 24.14±0.20°, and 27.69±0.20°.

In some embodiments of the present invention, the crystal form A has an XRPD pattern with characteristic diffraction peaks at 2θ of 5.402°, 8.949°, 10.766°, 11.989°, 13.186°, 14.766°, 16.090°, 16.779°, 19.721°, 21.554°, 23.251°, 23.685°, 24.138°, 25.224°, 27.690°, 28.670°, 29.287°, 31.378°, 33.941°, and 38.046°.

In some embodiments of the present invention, the crystal form A has an XRPD as shown in FIG. 1.

In some embodiments of the present invention, the resolved data from the XRPD pattern of the crystal form A are shown in Table 1:

TABLE 1

Resolved data from the XRPD pattern of the crystal form A

| No. | 2θ (°) | Interplanar spacing (Å) | Relative intensity (%) | No. | 2θ (°) | Interplanar spacing (Å) | Relative intensity (%) |
|---|---|---|---|---|---|---|---|
| 1 | 5.402 | 16.3462 | 100.0 | 11 | 23.251 | 3.8224 | 49.7 |
| 2 | 8.949 | 9.8734 | 15.1 | 12 | 23.685 | 37534 | 31.9 |
| 3 | 10.766 | 8.2108 | 62.3 | 13 | 24.138 | 3.6839 | 43.7 |
| 4 | 11.989 | 7.3758 | 98.4 | 14 | 25.224 | 3.5278 | 13.6 |
| 5 | 13.186 | 6.7087 | 16.2 | 15 | 27.690 | 3.2189 | 28.3 |
| 6 | 14.766 | 5.9943 | 99.6 | 16 | 28.670 | 3.1111 | 8.1 |
| 7 | 16.090 | 5.5040 | 17.2 | 17 | 29.287 | 3.0469 | 12.0 |
| 8 | 16.779 | 5.2794 | 18.0 | 18 | 31.378 | 2.8485 | 8.1 |
| 9 | 19.721 | 4.4980 | 148 | 19 | 33.941 | 2.6391 | 7.5 |
| 10 | 21.554 | 4.1195 | 55.7 | 20 | 38.046 | 2.3632 | 6.9 |

In some embodiments of the present invention, the crystal form A has a differential scanning calorimetry (DSC) profile with an endothermic peak starting at 220.0±3.0° C.

In some embodiments of the present invention, the crystal form A has a DSC profile as shown in FIG. 2.

In some embodiments of the present invention, the crystal form A has a thermogravimetric analysis (TGA) curve showing a weight loss of 1.04% at 150.0° C.±3.0° C.

In some embodiments of the present invention, the crystal form A has a TGA curve as shown in FIG. 3.

The present invention further provides a crystal form B of the compound of Formula (II), having an XRPD pattern with characteristic diffraction peaks at 2θ of 14.89°±0.20°, 21.00°±0.20°, and 26.74°±0.20°.

In some embodiments of the present invention, the crystal form B has an XRPD pattern with characteristic diffraction peaks at 2θ of 12.07±0.20°, 14.89±0.20°, 21.00±0.20°, 21.70±0.20°, 24.34±0.20°, 26.74±0.20°, 27.59±0.20°, and 28.10±0.20°.

In some embodiments of the present invention, the crystal form B has an XRPD pattern with characteristic diffraction peaks at 2θ of 5.462°, 10.806°, 11.042°, 12.067°, 12.700°, 13.328°, 14.890°, 16.010°, 17.194°, 18.300°, 18.887°, 19.933°, 21.000°, 21.695°, 24.336°, 24.632°, 26.742°, 27.589°, 28.104°, 28.931°, 29.639°, 34.213°, and 35.560°.

In some embodiments of the present invention, the crystal form B has an XRPD pattern as shown in FIG. 4.

In some embodiments of the present invention, the resolved data from the XRPD pattern of the crystal form B are shown in Table 2:

TABLE 2

Resolved data from the XRPD pattern of the crystal form B

| No. | 2θ (°) | Interplanar spacing (Å) | Relative intensity (%) |
|---|---|---|---|
| 1 | 5.462 | 16.1654 | 8.5 |
| 2 | 10.806 | 8.1808 | 11.5 |
| 3 | 11.042 | 8.0061 | 15.4 |
| 4 | 12.067 | 7.3282 | 28.5 |
| 5 | 12.700 | 6.9642 | 14.6 |
| 6 | 13.328 | 6.6378 | 16.2 |
| 7 | 14.890 | 5.9447 | 28.5 |
| 8 | 16.010 | 5.5311 | 17.9 |
| 9 | 17.194 | 5.1529 | 15.4 |
| 10 | 18.300 | 4.8440 | 14.3 |
| 11 | 18.887 | 4.6946 | 8.8 |
| 12 | 19.933 | 4.4507 | 15.6 |
| 13 | 21.000 | 4.2268 | 100.0 |
| 14 | 21.695 | 4.0930 | 25.8 |
| 15 | 24.336 | 3.6545 | 26.4 |
| 16 | 24.632 | 3.6113 | 12.1 |
| 17 | 26.742 | 3.3309 | 36.0 |
| 18 | 27.589 | 3.2305 | 30.8 |
| 19 | 28.104 | 3.1725 | 27.0 |
| 20 | 28.931 | 3.0836 | 9.6 |
| 21 | 29.639 | 3.0116 | 18.6 |
| 22 | 34.213 | 2.6187 | 12.3 |
| 23 | 35.560 | 2.5225 | 11.0 |

The present invention further provides a crystal form C of the compound of Formula (II), having an XRPD pattern with characteristic diffraction peaks at 2θ of 23.21°±0.20°, 24.30°±0.20°, and 27.71°±0.20°.

In some embodiments of the present invention, the crystal form C has an XRPD pattern with characteristic diffraction peaks at 2θ of 5.16±0.20°, 10.25±0.20°, 13.76±0.20°, 15.42±0.20°, 23.21±0.20°, 24.30±0.20°, 26.43±0.20°, and 27.71±0.20°.

In some embodiments of the present invention, the crystal form C has an XRPD pattern with characteristic diffraction peaks at 2θ of 5.161°, 10.250°, 13.765°, 15.420°, 15.619°, 22.423°, 23.214°, 24.296°, 26.430°, 27.711°, 28.381°, 29.997°, and 31.376°.

In some embodiments of the present invention, the crystal form C has an XRPD pattern as shown in FIG. 5.

In some embodiments of the present invention, the resolved data from the XRPD pattern of the crystal form C are shown in Table 3:

TABLE 3

Resolved data from the XRPD pattern of the crystal form C

| No. | 2θ (°) | Interplanar spacing (Å) | Relative intensity (%) |
|---|---|---|---|
| 1 | 5.161 | 17.1094 | 42.4 |
| 2 | 10.250 | 8.6231 | 18.4 |
| 3 | 13.765 | 6.4280 | 26.8 |
| 4 | 15.420 | 5.7417 | 42.4 |
| 5 | 15.619 | 5.6689 | 43.2 |
| 6 | 22.423 | 3.9617 | 18.1 |
| 7 | 23.214 | 3.8286 | 100.0 |
| 8 | 24.296 | 3.6604 | 55.6 |
| 9 | 26.430 | 3.3695 | 19.2 |
| 10 | 27.711 | 3.2165 | 56.2 |
| 11 | 28.381 | 3.1421 | 18.6 |
| 12 | 29.997 | 2.9764 | 16.9 |
| 13 | 31.376 | 2.8487 | 15.5 |

The present invention further provides a crystal form D of the compound of Formula (II), having an XRPD pattern with characteristic diffraction peaks at 2θ of 12.17°±0.20°, 26.12°±0.20°, and 28.59°±0.20°.

In some embodiments of the present invention, the crystal form D has an XRPD pattern with characteristic diffraction peaks at 2θ of 6.05±0.20°, 12.17±0.20°, 13.35±0.20°, 19.65±0.20°, 26.12±0.20°, 27.50±0.20°, 28.59±0.20°, and 30.08±0.20°.

In some embodiments of the present invention, the crystal form D has an XRPD pattern with characteristic diffraction peaks at 2θ of 6.05°, 10.86°, 12.17°, 13.35°, 13.76°, 14.90°, 15.70°, 16.90°, 17.70°, 18.30°, 18.91°, 19.65°, 20.14°, 20.68°, 21.37°, 21.67°, 22.08°, 23.17°, 23.67°, 23.90°, 25.25°, 25.80°, 26.12°, 26.70°, 26.90°, 27.50°, 27.79°, 28.59°, 29.02°, 30.08°, 30.51°, 30.78°, 30.87°, 31.89°, 32.28°, 32.49°, 33.30°, 34.77°, 35.44°, 35.85°, 36.49°, 37.36°, 37.93°, and 38.96°.

In some embodiments of the present invention, the crystal form D has an XRPD pattern as shown in FIG. 6.

In some embodiments of the present invention, the resolved data from the XRPD pattern of the crystal form D are shown in Table 4:

TABLE 4

Resolved data from the XRPD pattern of the crystal form D

| No. | 2θ (°) | Interplanar spacing (Å) | Intensity (counts) | Relative intensity (%) |
|---|---|---|---|---|
| 1 | 6.05 | 14.60 | 1493.65 | 47.99 |
| 2 | 10.86 | 8.15 | 588.33 | 18.90 |
| 3 | 12.17 | 7.27 | 1586.82 | 50.98 |
| 4 | 13.35 | 6.63 | 1495.75 | 48.06 |
| 5 | 13.76 | 6.44 | 227.57 | 7.31 |
| 6 | 14.90 | 5.94 | 772.49 | 24.82 |
| 7 | 15.70 | 5.64 | 452.25 | 14.53 |
| 8 | 16.90 | 5.25 | 519.41 | 16.69 |
| 9 | 17.70 | 5.01 | 176.68 | 5.68 |
| 10 | 18.30 | 4.85 | 202.40 | 6.50 |
| 11 | 18.91 | 4.69 | 230.04 | 7.39 |
| 12 | 19.65 | 4.52 | 1199.00 | 38.52 |
| 13 | 20.14 | 4.41 | 247.92 | 7.97 |
| 14 | 20.68 | 4.30 | 192.33 | 6.18 |
| 15 | 21.37 | 4.16 | 433.82 | 13.94 |
| 16 | 21.67 | 4.10 | 349.50 | 11.23 |
| 17 | 22.08 | 4.03 | 745.99 | 23.97 |
| 18 | 23.17 | 3.84 | 975.67 | 31.35 |
| 19 | 23.67 | 3.76 | 594.30 | 19.09 |
| 20 | 23.90 | 3.72 | 379.58 | 12.20 |
| 21 | 25.25 | 3.53 | 356.43 | 11.45 |
| 22 | 25.80 | 3.45 | 985.66 | 31.67 |
| 23 | 26.12 | 3.41 | 3112.45 | 100.00 |
| 24 | 26.70 | 3.34 | 985.01 | 31.65 |
| 25 | 26.90 | 3.31 | 1201.29 | 38.60 |
| 26 | 27.50 | 3.24 | 1651.04 | 53.05 |
| 27 | 27.79 | 3.21 | 829.82 | 26.66 |
| 28 | 28.59 | 3.12 | 1847.45 | 59.36 |
| 29 | 29.02 | 3.08 | 325.63 | 10.46 |
| 30 | 30.08 | 2.97 | 141254 | 45.38 |
| 31 | 30.51 | 2.93 | 417.17 | 13.40 |
| 32 | 30.78 | 2.90 | 906.28 | 29.12 |
| 33 | 30.87 | 2.90 | 1070.89 | 34.41 |
| 34 | 31.89 | 2.81 | 291.97 | 9.38 |
| 35 | 32.28 | 277 | 602.81 | 19.37 |
| 36 | 32.49 | 2.76 | 421.98 | 13.56 |
| 37 | 33.30 | 2.69 | 370.55 | 11.91 |
| 38 | 34.77 | 2.58 | 618.82 | 19.88 |
| 39 | 35.44 | 2.53 | 168.05 | 5.40 |
| 40 | 35.85 | 2.50 | 222.73 | 7.16 |
| 41 | 36.49 | 2.46 | 134.82 | 4.33 |
| 42 | 37.36 | 2.41 | 137.95 | 4.43 |
| 43 | 37.93 | 2.37 | 174.27 | 5.60 |
| 44 | 38.96 | 2.31 | 157.68 | 5.07 |

The present invention further provides a crystal form E of the compound of Formula (II), having an XRPD pattern with characteristic diffraction peaks at 2θ of 13.10°±0.20°, 14.50°±0.20°, and 24.87°±0.20°.

In some embodiments of the present invention, the crystal form E has an XRPD pattern with characteristic diffraction peaks at 2θ of 10.64±0.20°, 13.10±0.20°, 14.50±0.20°, 15.77±0.20°, 17.47±0.20°, 21.57±0.20°, 24.87±0.20°, and 27.42±0.20°.

In some embodiments of the present invention, the crystal form E has an XRPD pattern with characteristic diffraction peaks at 2θ of 10.64°, 13.10°, 14.50°, 15.77°, 17.47°, 20.17°, 21.57°, 22.28°, 23.87°, 24.87°, 26.02°, 27.42°, 28.67°, 30.18°, and 31.52°.

In some embodiments of the present invention, the crystal form E has an XRPD pattern as shown in FIG. 7.

In some embodiments of the present invention, the resolved data from the XRPD pattern of the crystal form E are shown in Table 5:

TABLE 5

Resolved data from the XRPD pattern of the crystal form E

| No. | 2θ (°) | Interplanar spacing (Å) | Intensity (counts) | Relative intensity (%) |
|---|---|---|---|---|
| 1 | 10.64 | 8.31 | 165.99 | 34.62 |
| 2 | 13.10 | 6.76 | 479.52 | 100.00 |
| 3 | 14.50 | 6.11 | 389.62 | 81.25 |
| 4 | 15.77 | 5.62 | 124.41 | 25.94 |
| 5 | 17.47 | 5.08 | 164.15 | 34.23 |
| 6 | 20.17 | 4.40 | 116.33 | 24.26 |
| 7 | 21.57 | 4.12 | 202.48 | 42.23 |
| 8 | 22.28 | 3.99 | 124.02 | 25.86 |
| 9 | 23.87 | 3.73 | 99.05 | 20.66 |
| 10 | 24.87 | 3.58 | 277.14 | 57.80 |
| 11 | 26.02 | 3.42 | 96.88 | 20.20 |
| 12 | 27.42 | 3.25 | 159.52 | 33.27 |
| 13 | 28.67 | 3.11 | 75.69 | 15.79 |
| 14 | 30.18 | 2.96 | 62.87 | 13.11 |
| 15 | 31.52 | 2.84 | 63.01 | 13.14 |

The present invention further provides a crystal form F of the compound of Formula (II), having an XRPD pattern with characteristic diffraction peaks at 2θ of 5.44°±0.20°, 14.06°±0.20°, and 14.92°±0.20°.

In some embodiments of the present invention, the crystal form F has an XRPD pattern with characteristic diffraction peaks at 2θ of 5.44±0.20°, 5.95±0.20°, 10.80±0.20°, 13.50±0.20°, 14.06±0.20°, 14.92±0.20°, 19.38±0.20°, and 27.57±0.20°.

In some embodiments of the present invention, the crystal form F has an XRPD pattern with characteristic diffraction peaks at 2θ of 5.44°, 5.95°, 8.94°, 9.34°, 10.80°, 11.25°, 11.91°, 13.50°, 14.06°, 14.92°, 16.60°, 19.38°, 23.97°, 24.90°, 26.21°, and 27.57°.

In some embodiments of the present invention, the crystal form F has an XRPD pattern as shown in FIG. 8.

In some embodiments of the present invention, the resolved data from the XRPD pattern of the crystal form F are shown in Table 6:

TABLE 6

Resolved data from the XRPD pattern of the crystal form F

| No. | 2θ (°) | Interplanar spacing (Å) | Intensity (counts) | Relative intensity (%) |
|---|---|---|---|---|
| 1 | 5.44 | 16.26 | 675.57 | 97.93 |
| 2 | 5.95 | 14.87 | 354.67 | 51.41 |
| 3 | 8.94 | 9.90 | 141.47 | 20.51 |
| 4 | 9.34 | 9.47 | 177.07 | 25.67 |
| 5 | 10.80 | 8.19 | 299.64 | 43.44 |
| 6 | 11.25 | 7.87 | 46.93 | 6.80 |
| 7 | 11.91 | 7.43 | 127.00 | 18.41 |
| 8 | 13.50 | 6.56 | 198.78 | 28.82 |
| 9 | 14.06 | 6.30 | 689.84 | 100.00 |
| 10 | 14.92 | 5.94 | 612.42 | 88.78 |
| 11 | 16.60 | 5.34 | 73.65 | 10.68 |
| 12 | 19.38 | 4.58 | 369.80 | 53.61 |
| 13 | 23.97 | 3.71 | 129.94 | 18.84 |
| 14 | 24.90 | 3.58 | 111.85 | 16.21 |
| 15 | 26.21 | 3.40 | 93.51 | 13.56 |
| 16 | 27.57 | 3.24 | 207.39 | 30.06 |

The present invention provides a compound of Formula (III):

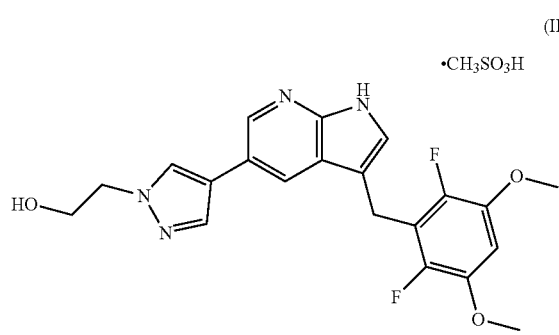

The present invention further provides a crystal form G of the compound of Formula (III), having an XRPD pattern with characteristic diffraction peaks at 2θ of 6.86°±0.20°, 7.53°±0.20°, and 15.46°±0.20°.

In some embodiments of the present invention, the crystal form G has an XRPD pattern with characteristic diffraction peaks at 2θ of 6.86±0.20°, 7.53±0.20°, 9.21±0.20°, 9.80±0.20°, 10.70±0.20°, 13.06±0.20°, 15.46±0.20°, and 20.53±0.20°.

In some embodiments of the present invention, the crystal form G has an XRPD pattern with characteristic diffraction peaks at 2θ of 6.859°, 7.532°, 9.211°, 9.799°, 10.704°, 13.057°, 13.525°, 14.847°, 15.029°, 15.461°, 17.473°, 18.656°, 19.382°, 19.585°, 20.235°, 20.528°, 20.805°, 21.158°, 21.420°, 22.109°, 22.604°, 23.368°, 23.663°, 24.058°, 24.356°, 25.203°, 26.822°, 27.157°, 27.571°, 28.601°, 28.970°, 29.583°, 30.223°, 32.483°, 34.552°, 34.748°, and 35.268°.

In some embodiments of the present invention, the crystal form G has an XRPD pattern as shown in FIG. 9.

In some embodiments of the present invention, the resolved data from the XRPD pattern of the crystal form G are shown in Table 7:

TABLE 7

Resolved data from the XRPD pattern of the crystal form G

| No. | 2θ (°) | Interplanar spacing (Å) | Relative intensity (%) |
|---|---|---|---|
| 1 | 6.859 | 12.8757 | 57.2 |
| 2 | 7.532 | 11.7279 | 100.0 |
| 3 | 9.211 | 9.5936 | 30.1 |
| 4 | 9.799 | 9.0187 | 49.3 |
| 5 | 10.704 | 8.2584 | 50.2 |
| 6 | 13.057 | 67747 | 30.5 |
| 7 | 13.525 | 6.5412 | 8.9 |
| 8 | 14.847 | 5.9617 | 5.8 |
| 9 | 15.029 | 5.8899 | 7.7 |
| 10 | 15.461 | 5.7265 | 61.5 |
| 11 | 17.473 | 5.0712 | 5.7 |
| 12 | 18.656 | 5.7524 | 9.0 |
| 13 | 19.382 | 4.5758 | 19.8 |
| 14 | 19.585 | 4.5290 | 17.2 |
| 15 | 20.235 | 4.3849 | 6.2 |
| 16 | 20.528 | 4.3229 | 25.3 |
| 17 | 20.805 | 4.2659 | 12.0 |
| 18 | 21.158 | 4.1957 | 5.3 |
| 19 | 21.420 | 4.1449 | 9.4 |
| 20 | 22.109 | 4.0173 | 20.4 |
| 21 | 22.604 | 3.9304 | 24.7 |
| 22 | 23.368 | 3.8036 | 20.5 |
| 23 | 23.663 | 3.7568 | 7.9 |
| 24 | 24.058 | 3.6961 | 9.0 |
| 25 | 24.356 | 3.6516 | 9.5 |
| 26 | 25.203 | 3.5306 | 8.3 |
| 27 | 26.822 | 3.3211 | 10.7 |
| 28 | 27.157 | 3.2809 | 11.2 |
| 29 | 27.571 | 3.2326 | 12.6 |
| 30 | 28.601 | 3.1184 | 12.2 |
| 31 | 28.970 | 3.0795 | 4.1 |
| 32 | 29.583 | 3.0171 | 9.5 |
| 33 | 30.223 | 2.9547 | 3.0 |
| 34 | 32.483 | 27541 | 9.1 |
| 35 | 34.552 | 2.5937 | 4.6 |
| 36 | 34.748 | 2.5796 | 3.6 |
| 37 | 35.268 | 2.5427 | 3.1 |

In some embodiments of the present invention, the crystal form G has a differential scanning calorimetry (DSC) profile with an endothermic peak starting at 47.3±3.0° C., 86.8±3.0° C., and 145.2±3.0° C. respectively.

In some embodiments of the present invention, the crystal form G has a DSC profile as shown in FIG. 10.

In some embodiments of the present invention, the crystal form G has a thermogravimetric analysis (TGA) curve showing a weight loss of 3.30% at 120.0° C.±3.0° C.

In some embodiments of the present invention, the crystal form G has a TGA curve as shown in FIG. 11.

The present invention further provides a crystal form H of the compound of Formula (III), having an XRPD pattern with characteristic diffraction peaks at 2θ of 7.49°±0.20°, 15.24°±0.20°, and 22.03°±0.20°.

In some embodiments of the present invention, the crystal form H has an XRPD pattern with characteristic diffraction peaks at 2θ of 6.76±0.20°, 7.49±0.20°, 9.16±0.20°, 10.73±0.20°, 13.09±0.20°, 15.24±0.20°, 20.17±0.20°, and 22.03±0.20°.

In some embodiments of the present invention, the crystal form H has an XRPD pattern with characteristic diffraction peaks at 2θ of 6.76±0.20°, 7.49±0.20°, 9.18±0.20°, 10.73±0.20°, 13.09±0.20°, 15.24±0.20°, 20.17±0.20°, and 22.03±0.20°.

In some embodiments of the present invention, the crystal form H has an XRPD pattern with characteristic diffraction peaks at 2θ of 6.761°, 7.493°, 9.165°, 9.917°, 10.728°, 12.701°, 13.092°, 13.405°, 15.243°, 18.264°, 19.600°, 20.173°, 20.489°, 22.030°, 24.280°, 27.037°, 29.843°, and 35.438°.

In some embodiments of the present invention, the crystal form H has an XRPD pattern as shown in FIG. 12.

In some embodiments of the present invention, the resolved data from the XRPD pattern of the crystal form H are shown in Table 8:

TABLE 8

Resolved data from the XRPD pattern of the crystal form H

| No. | 2θ (°) | Interplanar spacing (Å) | Relative intensity (%) |
|---|---|---|---|
| 1 | 6.761 | 13.0631 | 45.8 |
| 2 | 7.493 | 11.7883 | 87.0 |
| 3 | 9.165 | 9.6411 | 29.9 |
| 4 | 9.917 | 8.9115 | 46.3 |
| 5 | 10.728 | 8.2395 | 35.7 |
| 6 | 12.701 | 6.9642 | 15.1 |
| 7 | 13.092 | 6.7569 | 47.9 |
| 8 | 13.405 | 6.5997 | 24.0 |
| 9 | 15.243 | 5.8077 | 100.0 |
| 10 | 18.264 | 4.8535 | 16.0 |
| 11 | 19.600 | 4.5254 | 30.6 |
| 12 | 20.173 | 4.3982 | 39.1 |
| 13 | 20.489 | 4.3311 | 25.4 |
| 14 | 22.030 | 4.0315 | 67.6 |
| 15 | 24.280 | 3.6627 | 17.1 |
| 16 | 27.037 | 3.2952 | 15.3 |
| 17 | 29.843 | 2.9914 | 17.8 |
| 18 | 35.438 | 2.5309 | 16.2 |

The present invention further provides a crystal form I of the compound of Formula (III), having an XRPD pattern with characteristic diffraction peaks at 2θ of 6.85°±0.20°, 7.49°±0.20°, and 15.42°±0.20°.

In some embodiments of the present invention, the crystal form I has an XRPD pattern with characteristic diffraction peaks at 2θ of 6.85±0.20°, 7.49±0.20°, 9.80±0.20°, 10.69±0.20°, 13.06±0.20°, 15.42±0.20°, 20.53±0.20°, and 22.64±0.20°.

In some embodiments of the present invention, the crystal form I has an XRPD pattern with characteristic diffraction peaks at 2θ of 6.854°, 7.494°, 9.171°, 9.797°, 10.688°, 13.055°, 14.810°, 15.422°, 18.676°, 19.383°, 19.620°, 20.527°, 20.881°, 22.105°, 22.640°, 23.389°, 24.094°, 24.356°, 25.185°, 26.802°, 27.432°, 28.633°, 29.561°, and 32.466°.

In some embodiments of the present invention, the crystal form I has an XRPD pattern as shown in FIG. 13.

In some embodiments of the present invention, the resolved data from the XRPD pattern of the crystal form I are shown in Table 9:

TABLE 9

Resolved data from the XRPD pattern of the crystal form I

| No. | 2θ (°) | Interplanar spacing (Å) | Relative intensity (%) |
|---|---|---|---|
| 1 | 6.854 | 12.8857 | 58.4 |
| 2 | 7.494 | 11.7863 | 100.0 |
| 3 | 9.171 | 9.6346 | 31.8 |
| 4 | 9.797 | 9.0202 | 56.5 |
| 5 | 10.688 | 8.2709 | 51.4 |
| 6 | 13.055 | 6.7758 | 40.9 |
| 7 | 14.810 | 5.9766 | 9.4 |

TABLE 9-continued

Resolved data from the XRPD pattern of the crystal form I

| No. | 2θ (°) | Interplanar spacing (Å) | Relative intensity (%) |
|---|---|---|---|
| 8 | 15.422 | 57409 | 69.9 |
| 9 | 18.676 | 4.7473 | 17.8 |
| 10 | 19.383 | 4.5757 | 24.3 |
| 11 | 19.620 | 4.5209 | 24.3 |
| 12 | 20.527 | 4.3232 | 36.4 |
| 13 | 20.881 | 4.2507 | 19.0 |
| 14 | 22.105 | 4.0181 | 28.2 |
| 15 | 22.640 | 3.9243 | 40.8 |
| 16 | 23.389 | 3.8003 | 29.9 |
| 17 | 24.094 | 3.6906 | 9.5 |
| 18 | 24.356 | 3.6515 | 13.8 |
| 19 | 25.185 | 3.5332 | 13.1 |
| 20 | 26.802 | 3.3236 | 16.9 |
| 21 | 27.432 | 3.2486 | 20.5 |
| 22 | 28.633 | 3.1151 | 18.4 |
| 23 | 29.561 | 3.0193 | 13.0 |
| 24 | 32.466 | 2.7555 | 12.9 |

The present invention provides a compound of Formula (IV):

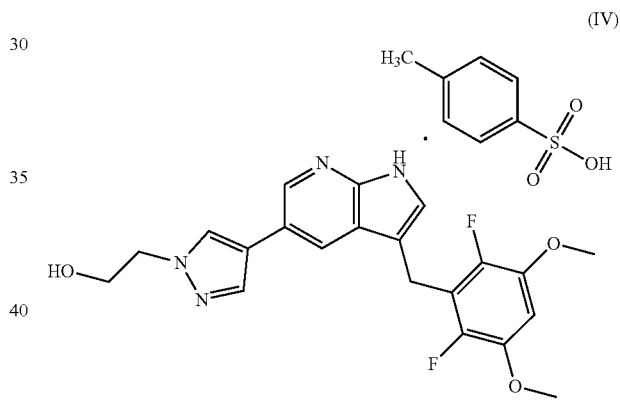

(IV)

The present invention further provides a crystal form J of the compound of Formula (IV), having an XRPD pattern with characteristic diffraction peaks at 2θ of 4.59°±0.20°, 7.02°±0.20°, and 18.05°±0.20°.

In some embodiments of the present invention, the crystal form J has an XRPD pattern with characteristic diffraction peaks at 2θ of 4.59±0.20°, 7.02±0.20°, 10.13±0.20°, 14.06±0.20°, 18.05±0.20°, 19.82±0.20°, 22.56±0.20°, and 27.04±0.20°.

In some embodiments of the present invention, the crystal form J has an XRPD pattern with characteristic diffraction peaks at 2θ of 4.592°, 6.094°, 7.018°, 9.383°, 10.132°, 11.535°, 12.241°, 14.059°, 18.046°, 19.819°, 21.435°, 22.561°, 23.764°, 24.117°, 26.489°, 27.035°, 28.732°, and 36.524°.

In some embodiments of the present invention, the crystal form J has an XRPD pattern as shown in FIG. 14.

In some embodiments of the present invention, the resolved data from the XRPD pattern of the crystal form J are shown in Table 10:

TABLE 10

Resolved data from the XRPD pattern of the crystal form J

| No. | 2θ (°) | Interplanar spacing (Å) | Relative intensity (%) |
|---|---|---|---|
| 1 | 4.592 | 19.2263 | 100.0 |
| 2 | 6.094 | 14.4902 | 2.1 |
| 3 | 7.018 | 12.5850 | 23.8 |
| 4 | 9.383 | 9.4181 | 1.4 |
| 5 | 10.132 | 8.7228 | 2.8 |
| 6 | 11.535 | 7.6653 | 2.5 |
| 7 | 12.241 | 7.2247 | 1.3 |
| 8 | 14.059 | 6.2942 | 10.1 |
| 9 | 18.046 | 4.9115 | 14.0 |
| 10 | 19.819 | 4.4759 | 5.7 |
| 11 | 21.435 | 4.1420 | 1.6 |
| 12 | 22.561 | 3.9377 | 4.3 |
| 13 | 23.764 | 3.7411 | 1.7 |
| 14 | 24.117 | 3.6871 | 2.7 |
| 15 | 26.489 | 3.3621 | 1.3 |
| 16 | 27.035 | 3.2954 | 3.3 |
| 17 | 28.732 | 3.1045 | 2.5 |
| 18 | 36.524 | 2.4581 | 1.2 |

In some embodiments of the present invention, the crystal form J has a thermogravimetric analysis (TGA) curve showing a weight loss of 4.97% at 120.0° C.±3.0° C.

In some embodiments of the present invention, the crystal form J has a TGA curve as shown in FIG. 15.

The present invention further provides a crystal form K of the compound of Formula (IV), having an XRPD pattern with characteristic diffraction peaks at 2θ of 4.57°±0.20°, 18.02°±0.20°, and 19.76°±0.20°.

In some embodiments of the present invention, the crystal form K has an XRPD pattern with characteristic diffraction peaks at 2θ of 4.57±0.20°, 6.98±0.20°, 12.68±0.20°, 13.98±0.20°, 18.02±0.20°, 19.76±0.20°, 22.56±0.20°, and 26.96±0.20°.

In some embodiments of the present invention, the crystal form K has an XRPD pattern with characteristic diffraction peaks at 2θ of 4.570°, 6.111°, 6.980°, 9.069°, 10.173°, 11.023°, 11.591°, 12.680°, 13.980°, 15.953°, 17.119°, 18.024°, 19.760°, 20.213°, 20.942°, 21.419°, 22.560°, 24.081°, 24.611°, 26.960°, 28.121°, 28.575°, 29.640°, 31.733°, and 36.329°.

In some embodiments of the present invention, the crystal form K has an XRPD pattern as shown in FIG. 16.

In some embodiments of the present invention, the resolved data from the XRPD pattern of the crystal form K are shown in Table 11:

TABLE 11

Resolved data from the XRPD pattern of the crystal form K

| No. | 2θ (°) | Interplanar spacing (Å) | Relative intensity (%) |
|---|---|---|---|
| 1 | 4.570 | 19.3192 | 100.0 |
| 2 | 6.111 | 14.4499 | 3.0 |
| 3 | 6.980 | 12.6539 | 15.2 |
| 4 | 9.069 | 9.7426 | 4.5 |
| 5 | 10.173 | 8.6879 | 2.8 |
| 6 | 11.023 | 8.0197 | 3.7 |
| 7 | 11.591 | 7.6279 | 4.6 |
| 8 | 12.680 | 6.9756 | 7.3 |
| 9 | 13.980 | 6.3293 | 8.3 |
| 10 | 15.953 | 5.5510 | 3.0 |
| 11 | 17.119 | 5.1754 | 5.4 |
| 12 | 18.024 | 4.9174 | 41.5 |
| 13 | 19.760 | 4.4892 | 19.8 |
| 14 | 20.213 | 4.3897 | 5.6 |
| 15 | 20.942 | 4.2384 | 5.0 |
| 16 | 21.419 | 4.1451 | 3.3 |
| 17 | 22.560 | 3.9380 | 12.2 |
| 18 | 24.081 | 3.6925 | 6.7 |
| 19 | 24.611 | 3.6143 | 5.6 |
| 20 | 26.960 | 3.3045 | 7.2 |
| 21 | 28.121 | 3.1706 | 3.5 |
| 22 | 28.575 | 3.1212 | 4.4 |
| 23 | 29.640 | 3.0114 | 2.5 |
| 24 | 31.733 | 2.8175 | 2.5 |
| 25 | 36.329 | 2.4708 | 3.7 |

The present invention further provides a crystal form L of the compound of Formula (IV), having an XRPD pattern with characteristic diffraction peaks at 2θ of 4.61°±0.20°, 7.02°±0.20°, and 18.28°±0.20°.

In some embodiments of the present invention, the crystal form L has an XRPD pattern with characteristic diffraction peaks at 2θ of 4.61±0.20°, 7.02±0.20°, 11.83±0.20°, 18.28±0.20°, 20.27±0.20°, 21.50±0.20°, 22.58±0.20°, and 26.96±0.20°.

In some embodiments of the present invention, the crystal form L has an XRPD pattern with characteristic diffraction peaks at 2θ of 4.611°, 5.006°, 7.018°, 9.129°, 11.829°, 12.246°, 14.016°, 18.279°, 18.733°, 20.272°, 20.904°, 21.495°, 22.578°, 24.554°, 25.517°, 26.959°, 28.990°, and 29.603°.

In some embodiments of the present invention, the crystal form L has an XRPD pattern as shown in FIG. 17.

In some embodiments of the present invention, the resolved data from the XRPD pattern of the crystal form L are shown in Table 12:

TABLE 12

Resolved data from the XRPD pattern of the crystal form L

| No. | 2θ (°) | Interplanar spacing (Å) | Relative intensity (%) |
|---|---|---|---|
| 1 | 4.611 | 19.1486 | 100.0 |
| 2 | 5.006 | 17.6369 | 32.5 |
| 3 | 7.018 | 12.5852 | 52.7 |
| 4 | 9.129 | 9.6797 | 7.6 |
| 5 | 11.829 | 7.4750 | 12.6 |
| 6 | 12.246 | 7.2219 | 7.5 |
| 7 | 14.016 | 6.3135 | 11.6 |
| 8 | 18.279 | 4.8494 | 55.0 |
| 9 | 18.733 | 4.7329 | 15.5 |
| 10 | 20.272 | 4.3770 | 21.3 |
| 11 | 20.904 | 4.2460 | 10.2 |
| 12 | 21.495 | 4.1306 | 49.7 |
| 13 | 22.578 | 3.9348 | 29.2 |
| 14 | 24.554 | 3.6225 | 16.9 |
| 15 | 25.517 | 3.4879 | 8.7 |
| 16 | 26.959 | 3.3046 | 23.5 |
| 17 | 28.990 | 3.0775 | 12.9 |
| 18 | 29.603 | 3.0151 | 13.3 |

The present invention further provides a crystal form M of the compound of Formula (I), having an XRPD pattern with characteristic diffraction peaks at 2θ of 5.77°±0.20°, 12.63°±0.20°, and 15.40°±0.20°.

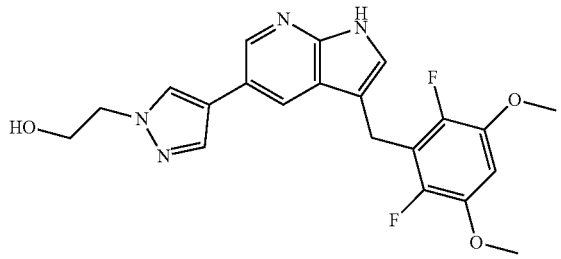

(I)

In some embodiments of the present invention, the crystal form M has an XRPD pattern with characteristic diffraction peaks at 2θ of 5.77±0.20°, 11.59±0.20°, 12.63±0.20°, 15.40±0.20°, 16.42±0.20°, 20.77±0.20°, 22.62±0.20°, and 23.36±0.20°.

In some embodiments of the present invention, the crystal form M has an XRPD pattern with characteristic diffraction peaks at 2θ of 5.77°, 5.95°, 10.52°, 11.59°, 12.63°, 13.12°, 15.40°, 16.42°, 16.94°, 18.05°, 20.03°, 20.77°, 21.44°, 22.62°, 22.98°, 23.36°, 24.46°, 25.82°, 26.54°, 27.31°, 27.96°, 29.70°, 31.17°, 32.04°, 33.16°, and 35.45°.

In some embodiments of the present invention, the crystal form M has an XRPD pattern as shown in FIG. 18.

In some embodiments of the present invention, the resolved data from the XRPD pattern of the crystal form M are shown in Table 13:

TABLE 13

Resolved data from the XRPD pattern of the crystal form M

| No. | 2θ (°) | Interplanar spacing (Å) | Intensity (counts) | Relative intensity (%) |
|---|---|---|---|---|
| 1 | 5.77 | 15.32 | 3437.28 | 44.97 |
| 2 | 5.95 | 14.87 | 2932.55 | 38.37 |
| 3 | 10.52 | 8.41 | 367.14 | 4.80 |
| 4 | 11.59 | 7.64 | 1696.52 | 22.20 |
| 5 | 12.63 | 7.01 | 2283.38 | 29.87 |
| 6 | 13.12 | 6.75 | 183.61 | 2.40 |
| 7 | 15.40 | 5.75 | 7643.69 | 100.00 |
| 8 | 16.42 | 5.40 | 860.98 | 11.26 |
| 9 | 16.94 | 5.23 | 277.21 | 3.63 |
| 10 | 18.05 | 4.92 | 494.53 | 6.47 |
| 11 | 20.03 | 4.43 | 356.48 | 4.66 |
| 12 | 20.77 | 4.28 | 783.70 | 10.25 |
| 13 | 21.44 | 4.14 | 359.06 | 4.70 |
| 14 | 22.62 | 3.93 | 652.45 | 8.54 |
| 15 | 22.98 | 3.87 | 505.62 | 6.61 |
| 16 | 23.36 | 3.81 | 924.34 | 12.09 |
| 17 | 24.46 | 3.64 | 155.16 | 2.03 |
| 18 | 25.82 | 3.45 | 353.20 | 4.62 |
| 19 | 26.54 | 3.36 | 618.93 | 8.10 |
| 20 | 27.31 | 3.27 | 160.35 | 2.10 |
| 21 | 27.96 | 3.19 | 141.66 | 1.85 |
| 22 | 2970 | 3.01 | 337.28 | 4.41 |
| 23 | 31.17 | 2.87 | 159.04 | 2.08 |
| 24 | 32.04 | 2.79 | 179.48 | 2.35 |
| 25 | 33.16 | 2.70 | 163.08 | 2.13 |
| 26 | 35.45 | 2.53 | 46.53 | 0.61 |

In some embodiments of the present invention, the crystal form M has a differential scanning calorimetry (DSC) profile with an endothermic peak starting at 74.4±3.0° C. and another endothermic peak starting at 214.3±3.0° C.

In some embodiments of the present invention, the crystal form M has a DSC profile as shown in FIG. 19.

In some embodiments of the present invention, the crystal form M has a thermogravimetric analysis (TGA) curve showing a weight loss of 7.54% at 120.0° C.±3.0° C.

In some embodiments of the present invention, the crystal form M has a TGA curve as shown in FIG. 20.

The present invention further provides a crystal form N of the compound of Formula (I), having an XRPD pattern with characteristic diffraction peaks at 2θ of 12.64°±0.20°, 17.10°±0.20°, and 20.92°±0.20°.

In some embodiments of the present invention, the crystal form N has an XRPD pattern with characteristic diffraction peaks at 2θ of 11.02±0.20°, 12.64±0.20°, 17.10±0.20°, 18.22±0.20°, 20.92±0.20°, 21.73±0.20°, 24.63±0.20°, and 26.65±0.20°.

In some embodiments of the present invention, the crystal form N has an XRPD pattern with characteristic diffraction peaks at 2θ of 9.111°, 11.022°, 12.642°, 13.289°, 15.934°, 16.626°, 17.096°, 18.221°, 18.753°, 19.876°, 20.234°, 20.922°, 21.733°, 22.659°, 22.972°, 24.631°, 25.416°, 25.776°, 26.646°, 27.454°, 28.103°, 28.360°, 28.835°, 29.561°, 32.683°, 34.041°, 35.459°, 36.959°, and 37.886°.

In some embodiments of the present invention, the crystal form N has an XRPD pattern as shown in FIG. 21.

In some embodiments of the present invention, the resolved data from the XRPD pattern of the crystal form N are shown in Table 14:

TABLE 14

Resolved data from the XRPD pattern of the crystal form N

| No. | 2θ (°) | Interplanar spacing (Å) | Relative intensity (%) |
|---|---|---|---|
| 1 | 9.111 | 9.6984 | 13.1 |
| 2 | 11.022 | 8.0205 | 32.5 |
| 3 | 12.642 | 6.9963 | 57.4 |
| 4 | 13.289 | 6.6571 | 26.4 |
| 5 | 15.934 | 5.5576 | 28.4 |
| 6 | 16.626 | 5.3277 | 11.4 |
| 7 | 17.096 | 5.1824 | 45.6 |
| 8 | 18.221 | 4.8648 | 33.8 |
| 9 | 18.753 | 4.7278 | 5.9 |
| 10 | 19.876 | 4.4632 | 25.8 |
| 11 | 20.234 | 4.3852 | 14.6 |
| 12 | 20.922 | 4.2423 | 100.0 |
| 13 | 21.733 | 4.0859 | 36.5 |
| 14 | 22.659 | 3.9210 | 16.4 |
| 15 | 22.972 | 3.8683 | 12.0 |
| 16 | 24.631 | 3.6114 | 45.6 |
| 17 | 25.416 | 3.5015 | 5.1 |
| 18 | 25.776 | 3.4535 | 11.3 |
| 19 | 26.646 | 3.3427 | 35.2 |
| 20 | 27.454 | 3.2461 | 26.6 |
| 21 | 28.103 | 3.1725 | 23.8 |
| 22 | 28.360 | 3.1444 | 5.9 |
| 23 | 28.835 | 3.0937 | 12.1 |
| 24 | 29.561 | 3.0194 | 18.7 |
| 25 | 32.683 | 2.7377 | 4.6 |
| 26 | 34.041 | 2.6315 | 5.3 |
| 27 | 35.459 | 2.5295 | 5.7 |
| 28 | 36.959 | 2.4302 | 4.9 |
| 29 | 37.886 | 2.3728 | 4.1 |

The present invention further provides a crystal form O of the compound of Formula (I), having an XRPD pattern with characteristic diffraction peaks at 2θ of 6.70°±0.20°, 10.41°±0.20°, and 13.74±0.20°.

In some embodiments of the present invention, the crystal form O has an XRPD pattern with characteristic diffraction peaks at 2θ of 4.63±0.20°, 6.70±0.20°, 9.80±0.20°, 10.41±0.20°, 13.74±0.20°, 14.16±0.20°, 16.57±0.20°, and 18.97±0.20°.

In some embodiments of the present invention, the crystal form O has an XRPD pattern with characteristic diffraction peaks at 2θ of 4.633°, 5.227°, 6.701°, 8.278°, 9.800°, 10.407°, 12.267°, 13.743°, 14.156°, 14.432°, 15.519°, 16.566°, 18.970°, 20.395°, and 24.479°.

In some embodiments of the present invention, the crystal form O has an XRPD pattern as shown in FIG. 22.

In some embodiments of the present invention, the resolved data from the XRPD pattern of the crystal form O are shown in Table 15:

TABLE 15

Resolved data from the XRPD pattern of the crystal form O

| No. | 2θ (°) | Interplanar spacing (Å) | Relative intensity (%) |
| --- | --- | --- | --- |
| 1 | 4.633 | 19.0585 | 43.8 |
| 2 | 5.227 | 16.8934 | 22.8 |
| 3 | 6.701 | 13.1801 | 97.6 |
| 4 | 8.278 | 10.6725 | 11.8 |
| 5 | 9.800 | 9.0182 | 84.1 |
| 6 | 10.407 | 8.4936 | 94.3 |
| 7 | 12.267 | 7.2096 | 11.3 |
| 8 | 13.743 | 6.4383 | 100.0 |
| 9 | 14.156 | 6.2511 | 31.5 |
| 10 | 14.432 | 6.1322 | 31.5 |
| 11 | 15.519 | 5.7050 | 14.8 |
| 12 | 16.566 | 5.3467 | 68.5 |
| 13 | 18.970 | 4.6742 | 38.2 |
| 14 | 20.395 | 4.3509 | 27.5 |
| 15 | 24.479 | 3.6335 | 15.3 |

The present invention further provides use of the compounds above, and use of the crystal form A, crystal form B, crystal form C, crystal form D, crystal form E, crystal form F, crystal form G, crystal form H, crystal form I, crystal form J, crystal form K, crystal form L, crystal form M, crystal form N or crystal form O of the compounds above in the preparation of medicine for treating FGFR and c-Met related diseases.

In some embodiments of the present invention, the medicine is used for the treatment of solid tumors.

Technical Effect

Various crystal form types of compounds of the present invention are stable and less affected by light, heat and humidity, have good therapeutic effect in vivo, thus having broad prospects in the preparation of drugs. Compared with the control, surprisingly, the crystal form A of the compound of Formula (II) has significantly improved activity against FGFR1 and FGFR4 and retains excellent activity against c-Met. The compounds of the present invention are obtained based on the structural analysis of the c-Met and FGFR kinase proteins, and a highly active small molecular nucleus that inhibits both c Met and FGFR is found. The compounds of the present invention are an inhibitor against dual targets of the c-Met and FGFR. The FGFR and c-Met targets are synergistic and complementary, and the FGFR mutation or c-Met mutation tend to have a signal compensation effect when the other is inhibited, thus making the tumor cells resistant to a single inhibitor. Such inhibitors against dual targets will potentially reduce tumor cell-dependent escape and greatly improve the effect of tumor treatment. Crystal form A of the compound of Formula (II) exhibits a moderately low clearance, a high volume of distribution, a moderate half-life, and a high level of drug exposure when administered intravenously. When administered orally, crystal form A of the compound of Formula (II) shows a rapid peak time, and a high level of oral exposure, where the exposure level was higher than that of the crystal form G of the compound of Formula (III), and the crystal form J of the compound of Formula (III). The crystal form A of the compound of Formula (II) exhibits an excellent tumor inhibitory effect in the tumor model SNU-16.

Definition

Unless otherwise specified, the following terms and phrases used herein are intended to have the following meanings. A particular phrase or term should not be considered uncertain or unclear unless specifically defined, but should be understood in its ordinary meaning. When a trade name appears herein, it is intended to refer to the corresponding product or active ingredient.

The intermediate compounds of the present invention can be prepared by a variety of synthesis methods well known to those skilled in the art, including the specific embodiments listed below, the embodiments formed by the combination of the listed synthesis methods with other chemical synthesis methods, and equivalent alternatives well-known to those skilled in the art. Preferred embodiments include, but are not limited to, the examples of the present invention.

The chemical reactions in specific embodiments of the present invention are carried out in solvents suitable for the chemical changes and dissolving required reagents and materials of the present invention. To obtain the compounds of the present invention, it is sometimes necessary for those skilled in the art to modify or select the synthetic steps or reaction schemes on the basis of the embodiments below.

The structure of the compound of the present invention can be determined by conventional methods well known to those skilled in the art, and if the present invention relates to the absolute configuration of the compound, the absolute configuration can be confirmed by conventional technical means in the art. For example, in single crystal X-ray diffraction (SXRD), the grown single crystal is collected for the diffraction intensity data by BrukerD8 venture diffractometer with a light source of CuKα radiation in a scanning mode of (φ/ω) scanning. After relevant data is collected, the crystal structure is further resolved by a direct method (Shelxs97), to determine the absolute configuration.

The present invention will be specifically described below through the specific embodiments, and these embodiments do not imply any limitation to the present invention.

All solvents used in the present invention are commercially available and used without further purification.

The solvents used in the present invention are commercially available. The following abbreviations are used in the present invention: EtOH represents ethanol; MeOH represents methanol; TFA represents trifluoroacetic acid; TsOH represents p-toluenesulfonic acid; mp represents melting point; THF represents tetrahydrofuran; EtOAc represents ethyl acetate; and Pd(dppf)Cl$_2$ represents [1,1' Bis(diphenylphosphino)ferrocene]palladium dichloride.

The compounds are named according to the conventional nomenclature in the art or by the ChemDraw® software, and the commercial compounds are named according to the directory name of the supplier.

X-Ray Powder Diffractometry (XRPD) of the Present Invention

Instrument model: X-ray powder diffractometer model X'Pert$^3$ from PANalytical

Test method: About 10 mg sample is used for XRPD detection.

Detailed XRPD Parameters:

Radiation source: Cu, kα (Kα1=1.540598 Å, Kα2=1.544426 Å, Kα2/Kα1 intensity ratio: 0.5)

Tube voltage: 45 kV, Tube current: 40 mA

Divergence slit: fixed ⅛ deg
First Soller slit: 0.04 rad, Second Soller slit: 0.04 rad
Receiving slit: No, Anti-scatter slit: 7.5 mm
Measurement time: 5 min
Sweep angle range: 3-40 deg
Step width: 0.0263 deg
Step length: 46.665 sec
Rotation speed of sample pan: 15 rpm
Differential Scanning Calorimetry (DSC) of the Present Invention
  Instrument model: TA5500 Differential Scanning Calorimeter
  Test method: A sample (about 1-5 mg) is placed in a DSC aluminum pan and tested at a flow rate of nitrogen of 50 mL/min, by heating the sample from 25° C. (room temperature) to the decomposition of the sample at a ramping rate of 10° C./min.
Thermal Gravimetric Analysis (TGA) of the Present Invention
  Instrument model: TA2500 Thermal Gravimetric Analyzer
  Test method: A sample (about 1-5 mg) is placed in a TGA aluminum pan and tested at a flow rate of nitrogen of 10 mL/min, by heating the sample from room temperature to 350° C. at a ramping rate of 10° C./min.
Dynamic Vapor Sorption (DVS) of the Present Invention
Instrument model: SMS DVS Intrinsic Dynamic Vapor Sorption Analyzer
  Test method: A sample (10-30 mg) is tested in a DVS sample pan.
  Detailed DVS Parameters:
  Temperature: 25° C.
  Equilibration: dm/dt=0.002%/min (Minimum: 10 min, Maximum: 180 min)
  RH (%) test interval: 10 (0-90%), 5 (90-95%)
  RH (%) test interval range: 0-95-0
  Hygroscopicity evaluations are classified as follows:

| Classification of hygroscopicity | ΔW % |
| --- | --- |
| Deliquescent | Absorb enough water to form a liquid |
| Highly hygroscopic | ΔW % ≥ 15% |
| Hygroscopic | 15% > ΔW % ≥ 2% |
| Slightly hygroscopic | 2% > ΔW % ≥ 0.2% |
| No or almost no hygroscopic | ΔW % < 0.2% |

Note: ΔW % represents the hygroscopic weight gain of the test product at 25° C./80% RH.

High Performance Liquid Chromatography (HPLC) of the Present Invention

| Compound content test and analysis method | |
| --- | --- |
| Chromatographic column | Waters Symmetry C18 (250 mm*4.6 mm, 5 μm) |
| Mobile phase A | 0.1% difluoroacetic acid in water |
| Mobile phase B | Acetonitrile |
| Diluent/needle wash | Acetonitrile: water = 1:1 |
| Flow rate | 1.0 mL/min |
| Volume of injection | 10 μL |
| Sample pan temperature | Not controlled |
| Column temperature | 40° C. |
| Detection wavelength | 230 nm |

| Compound content test and analysis method | | |
| --- | --- | --- |
| | Time (min) | Mobile phase A (%) | Mobile phase B (%) |
| Gradient elution program | 0 | 70 | 30 |
| | 10 | 70 | 30 |
| | 10.1 | 10 | 90 |
| | 15 | 10 | 90 |
| | 15.1 | 70 | 30 |
| | 25 | 70 | 30 |
| Test sample concentration | 0.1 mg/ml | | |
| Quantification method | External standard method | | |

DETAILED DESCRIPTION

Figure 1:
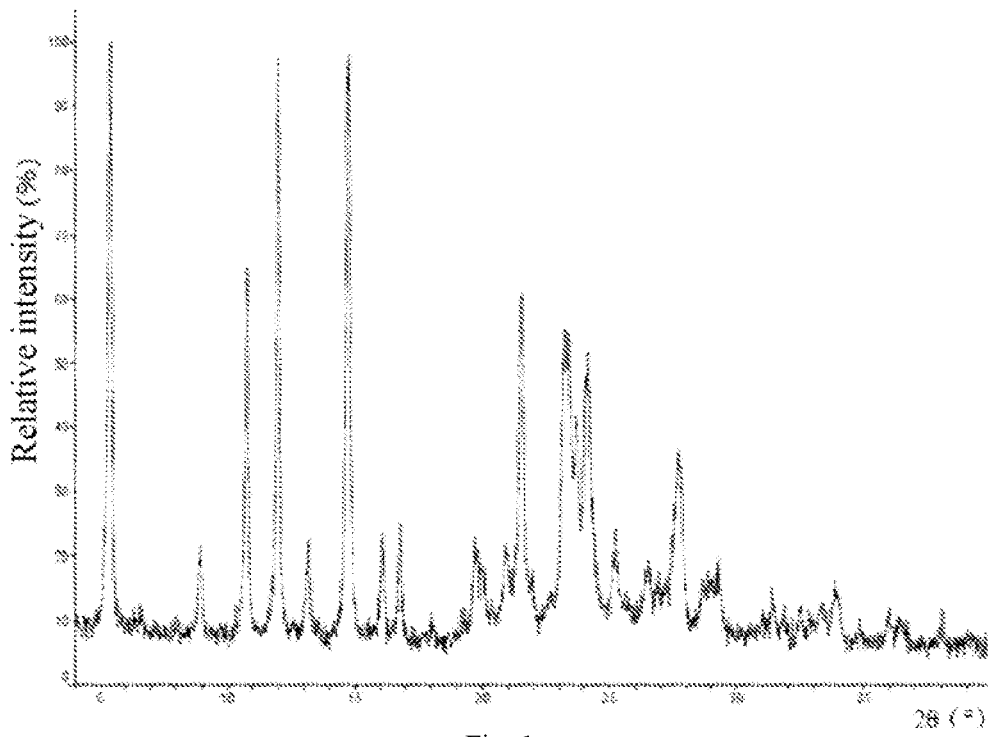
FIG. 1 is an XRPD pattern of the crystal form A of the compound of Formula (II) obtained using Cu-Kα radiation.
Figure 2:
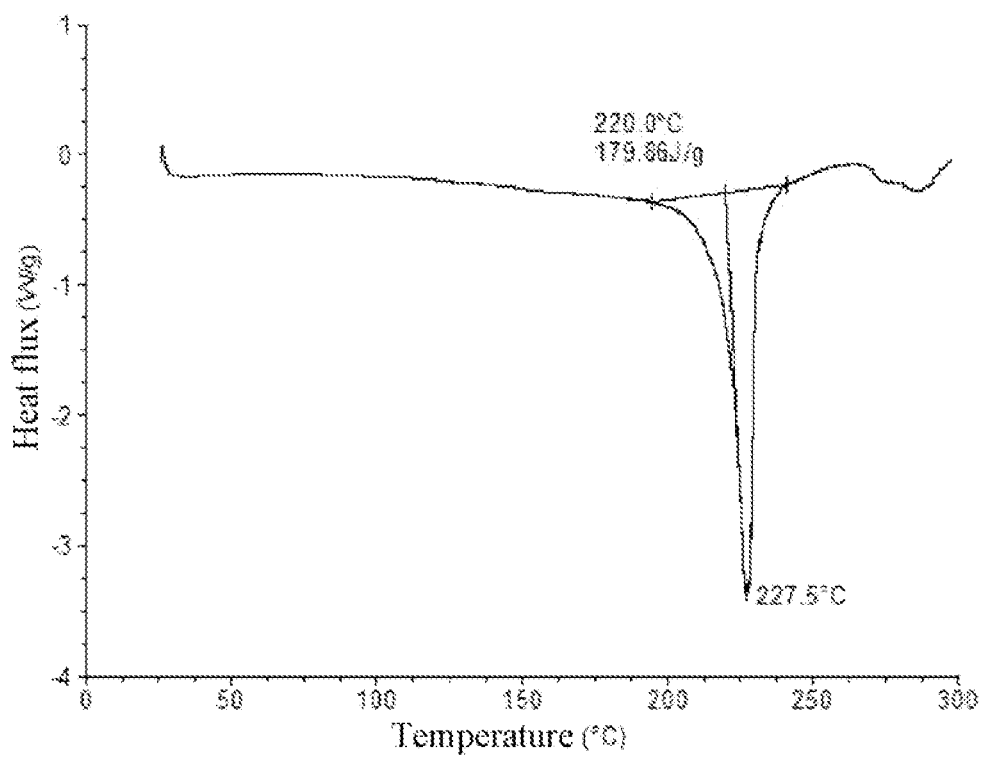
FIG. 2 is a DSC profile of the crystal form A of the compound of Formula (II).
Figure 3:
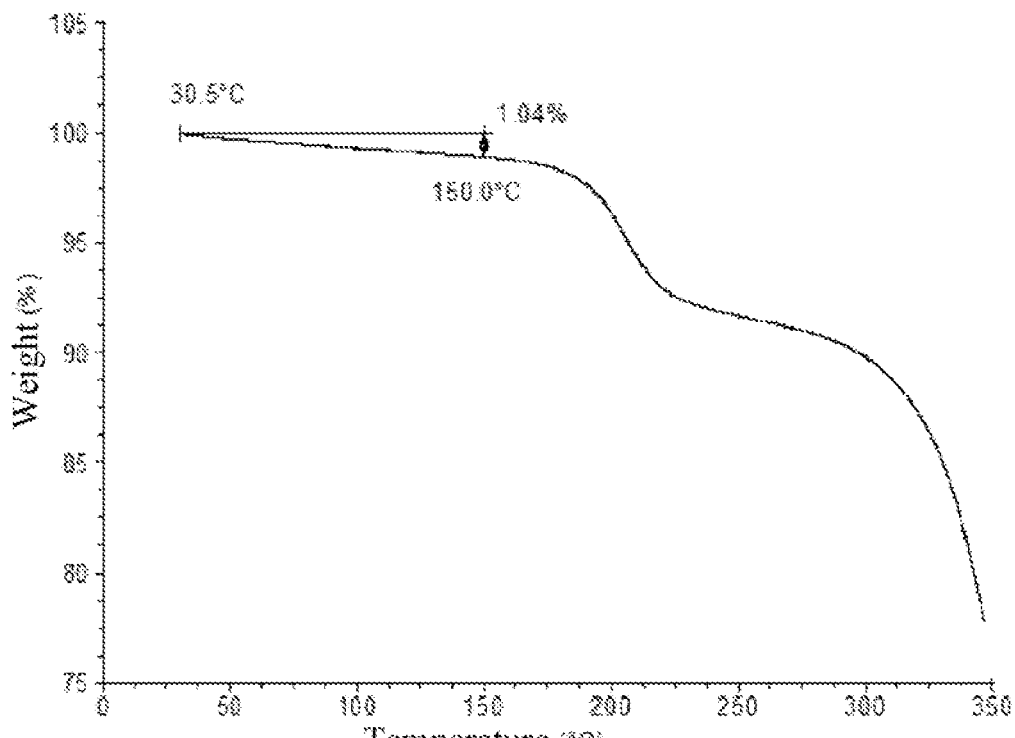
FIG. 3 is a TGA curve of the crystal form A of the compound of Formula (II).
Figure 4:
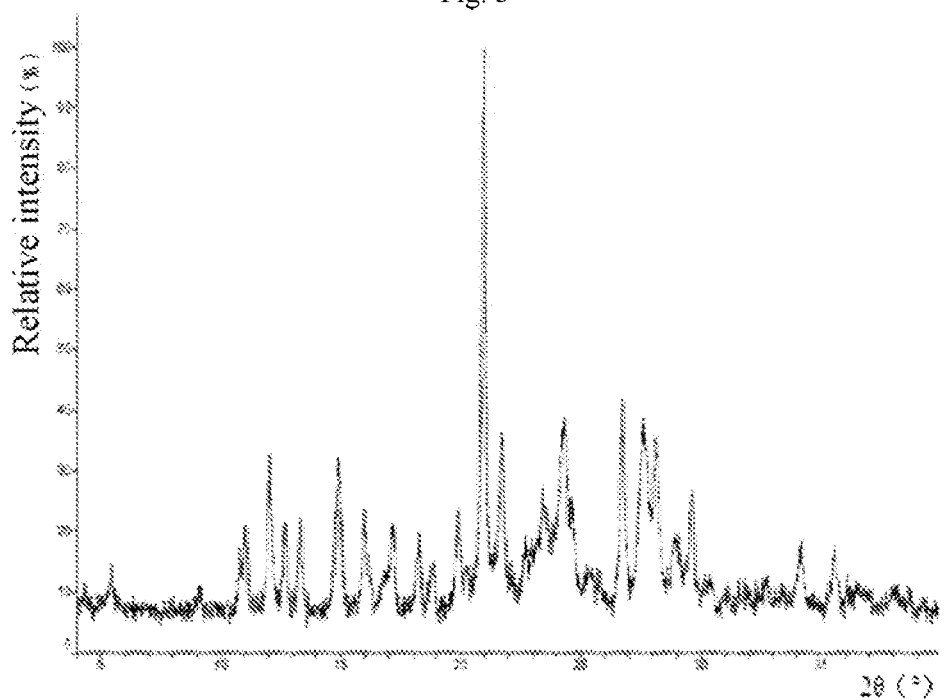
FIG. 4 is an XRPD pattern of the crystal form B of the compound of Formula (II) obtained using Cu-Kα radiation.
Figure 5:
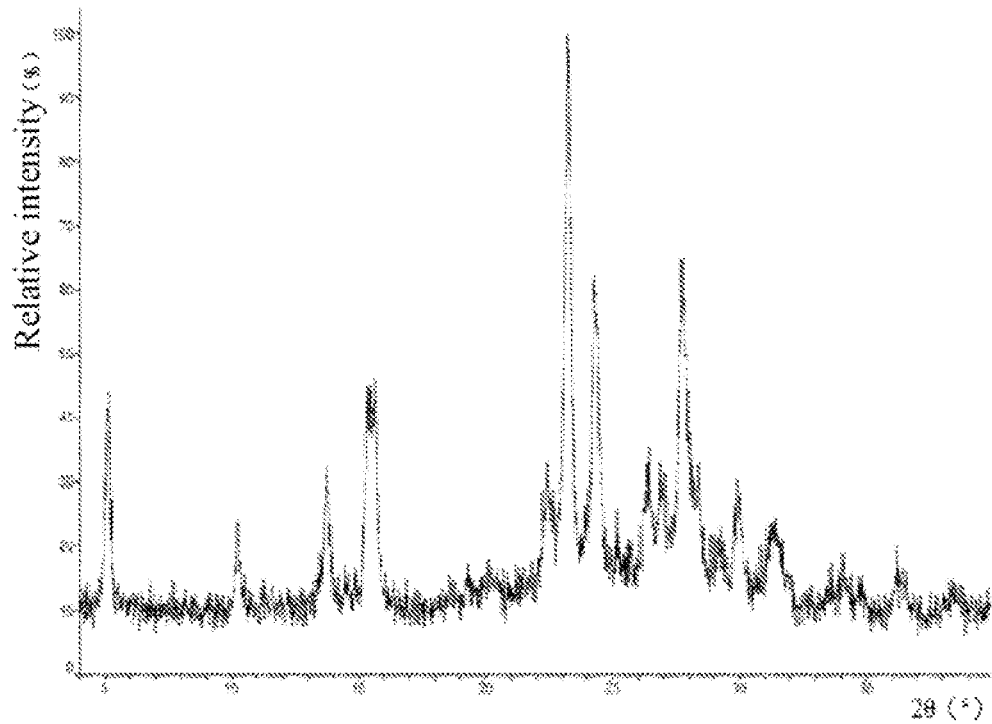
FIG. 5 is an XRPD pattern of the crystal form C of the compound of Formula (II) obtained using Cu-Kα radiation.
Figure 6:
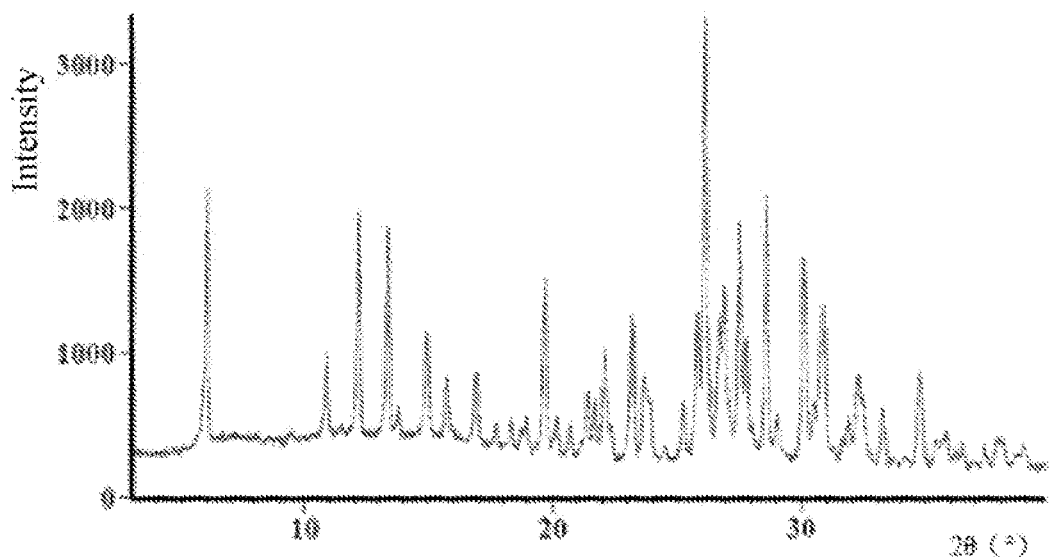
FIG. 6 is an XRPD pattern of the crystal form D of the compound of Formula (II) obtained using Cu-Kα radiation.
Figure 7:
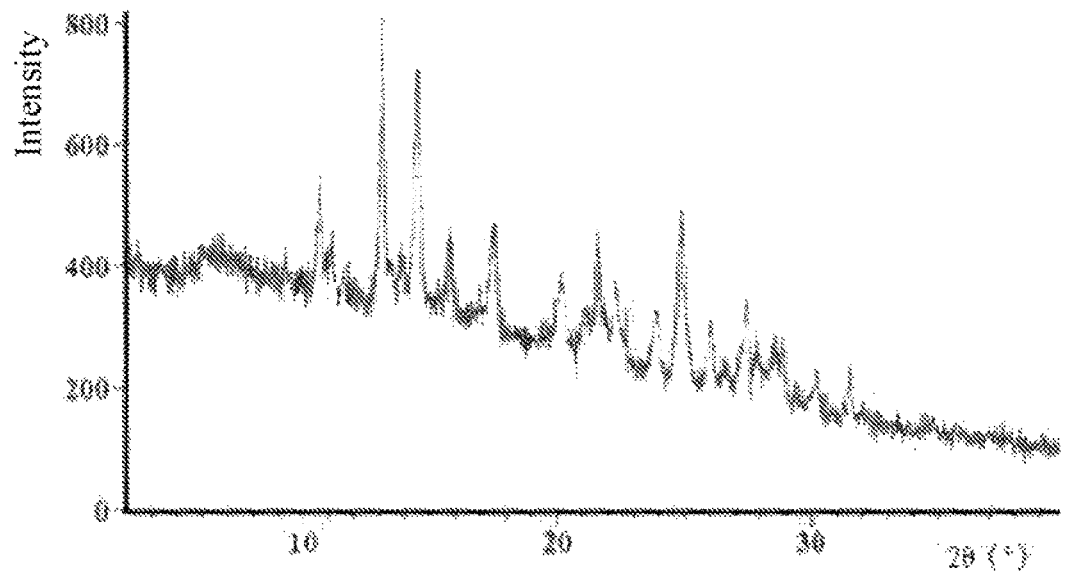
FIG. 7 is an XRPD pattern of the crystal form E of the compound of Formula (II) obtained using Cu-Kα radiation.
Figure 8:
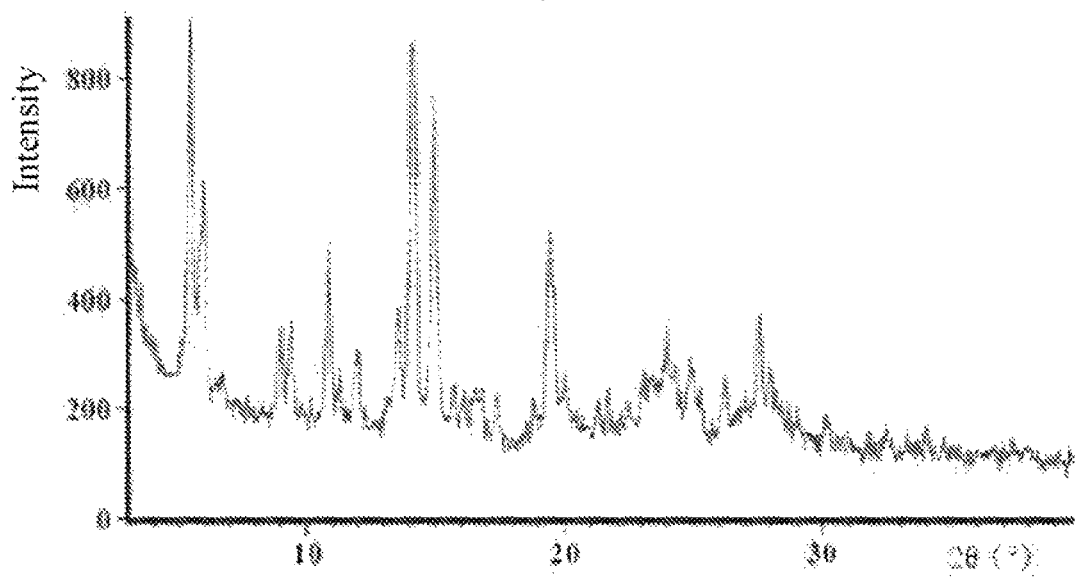
FIG. 8 is an XRPD pattern of the crystal form F of the compound of Formula (II) obtained using Cu-Kα radiation.
Figure 9:
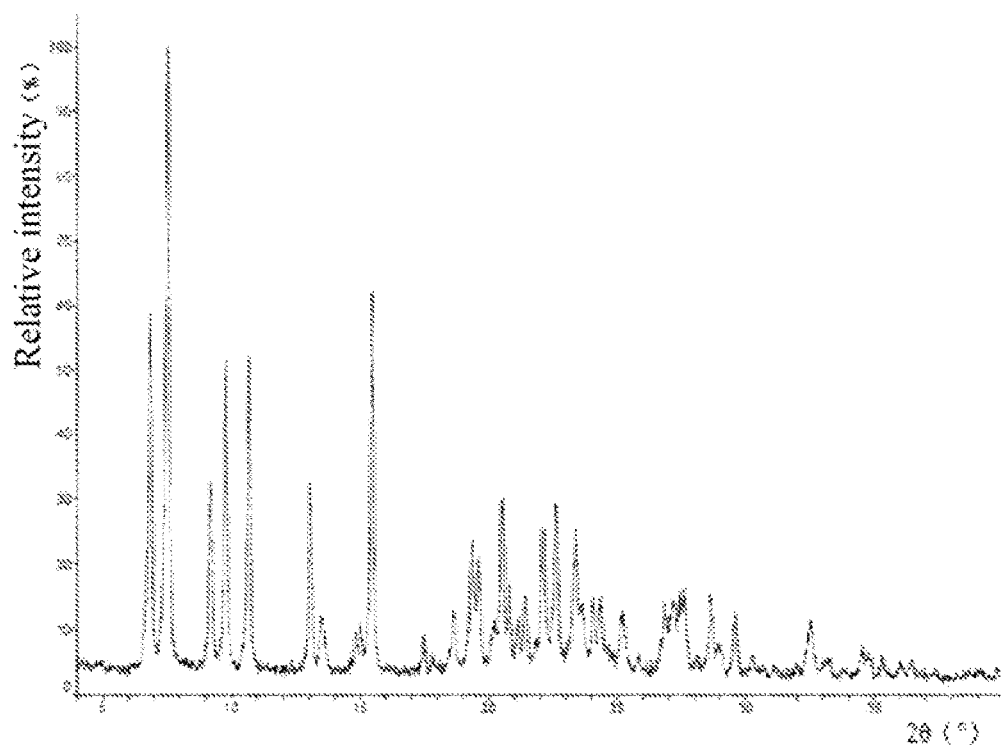
FIG. 9 is an XRPD pattern of the crystal form G of a compound of Formula (III) obtained using Cu-Kα radiation.
Figure 10:
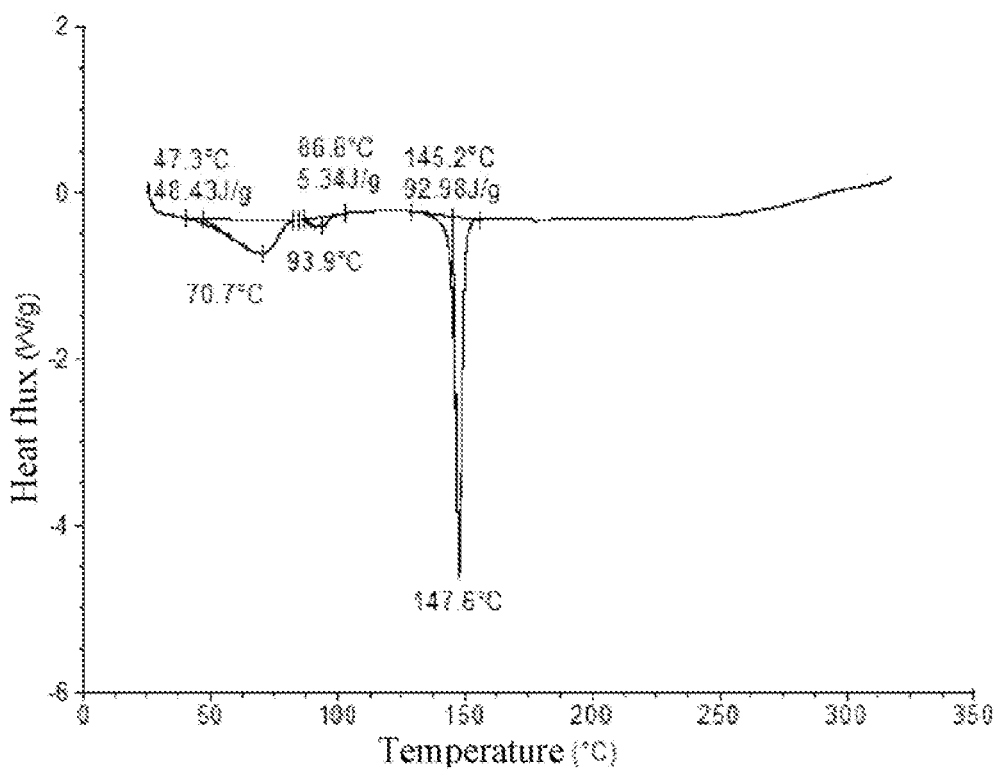
FIG. 10 is a DSC profile of the crystal form G of the compound of Formula (III).
Figure 11:
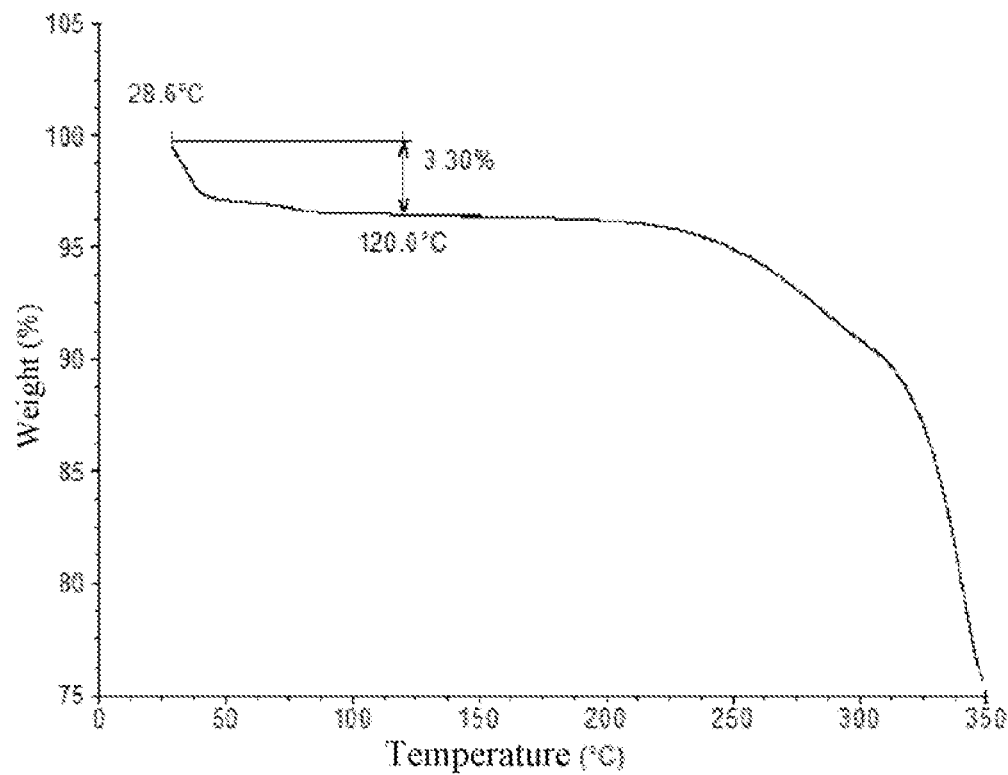
FIG. 11 is a TGA curve of the crystal form G of the compound of Formula (III).
Figure 12:
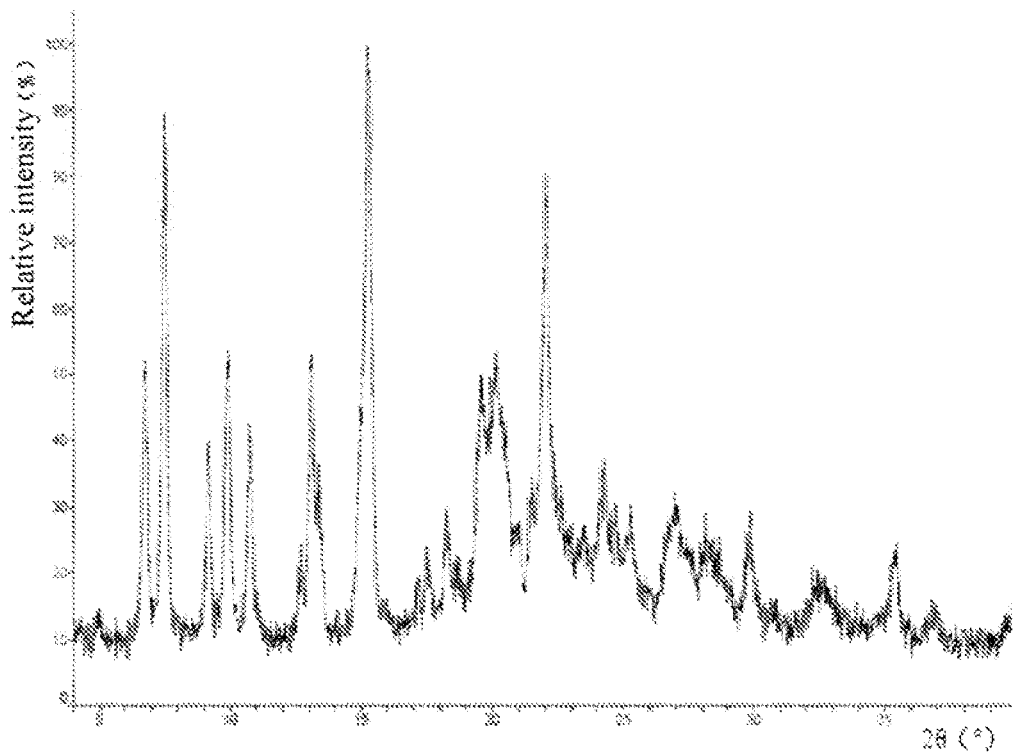
FIG. 12 is an XRPD pattern of the crystal form H of the compound of Formula (III) obtained using Cu-Kα radiation.
Figure 13:
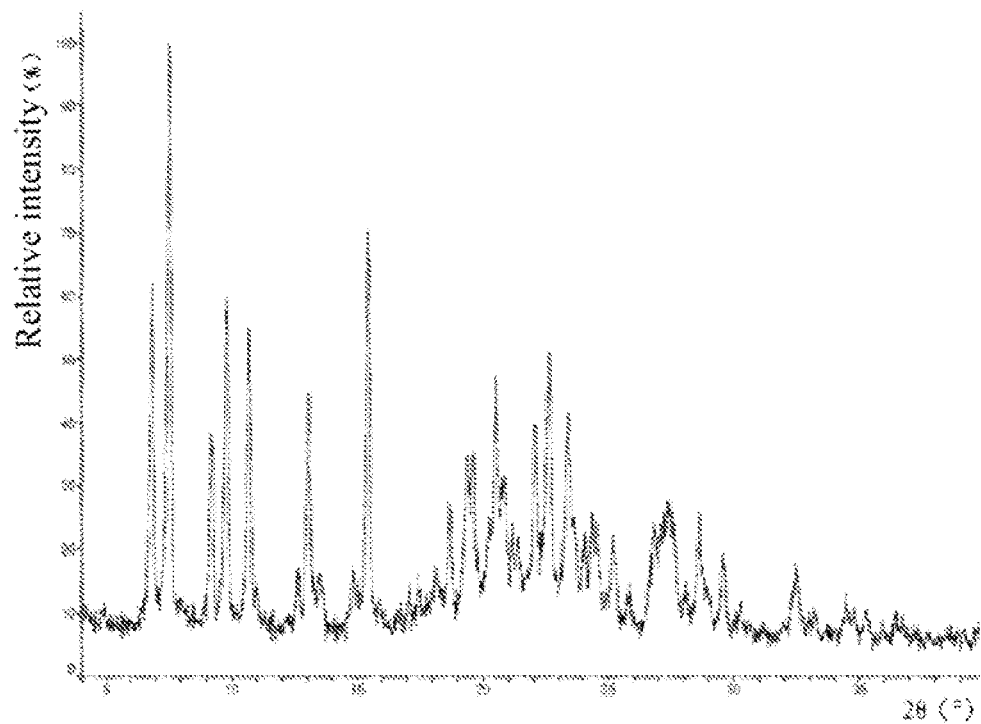
FIG. 13 is an XRPD pattern of the crystal form I of the compound of Formula (III) obtained using Cu-Kα radiation.
Figure 14:
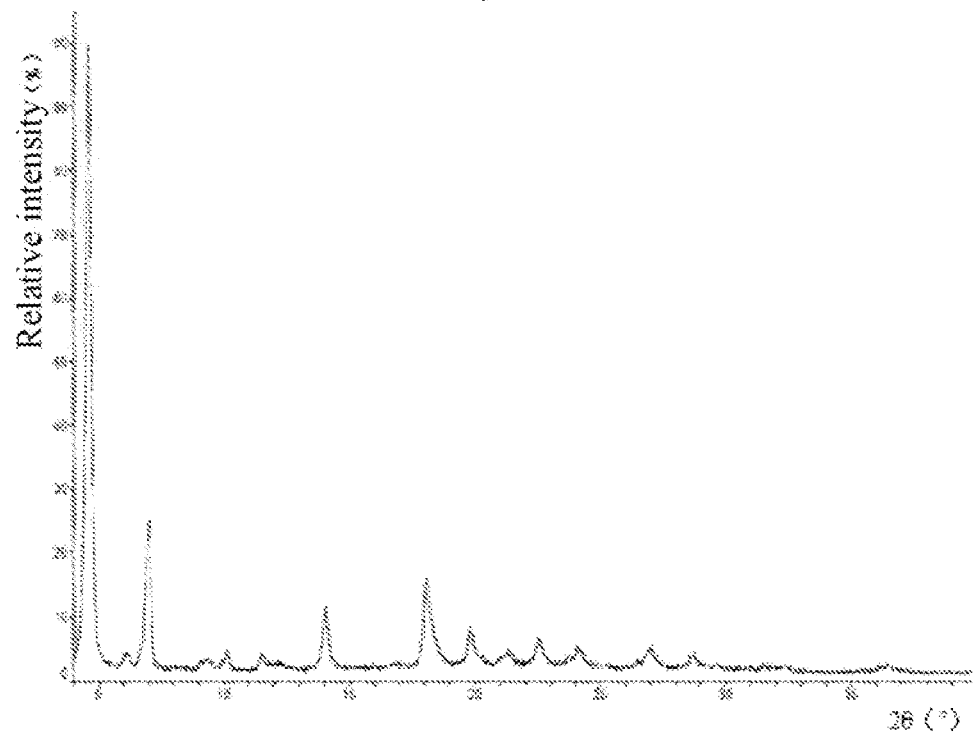
FIG. 14 is an XRPD pattern of the crystal form J of a compound of Formula (IV) obtained using Cu-Kα radiation.
Figure 15:
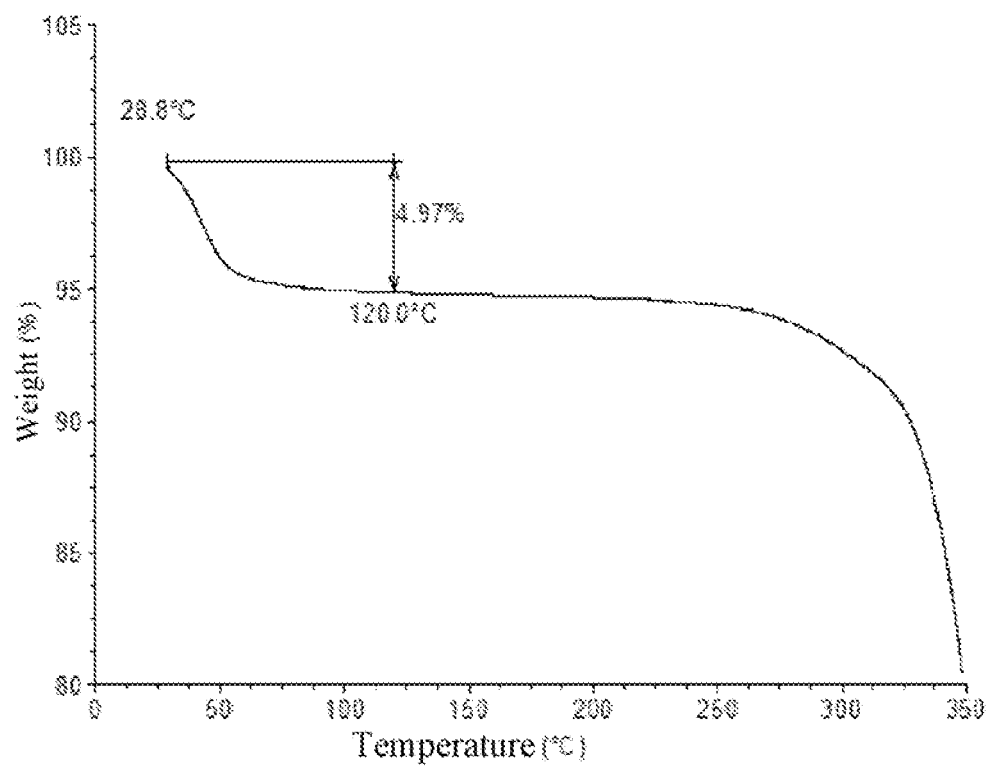
FIG. 15 is a TGA curve of the crystal form J of the compound of Formula (IV).
Figure 16:
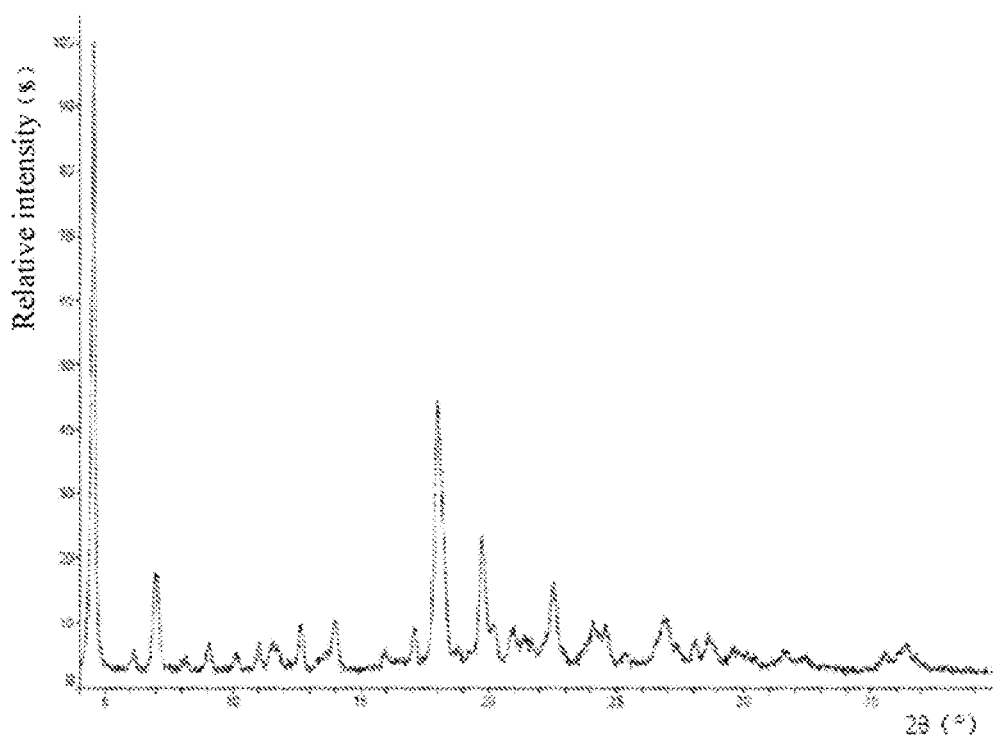
FIG. 16 is an XRPD pattern of the crystal form K of the compound of Formula (IV) obtained using Cu-Kα radiation.
Figure 17:
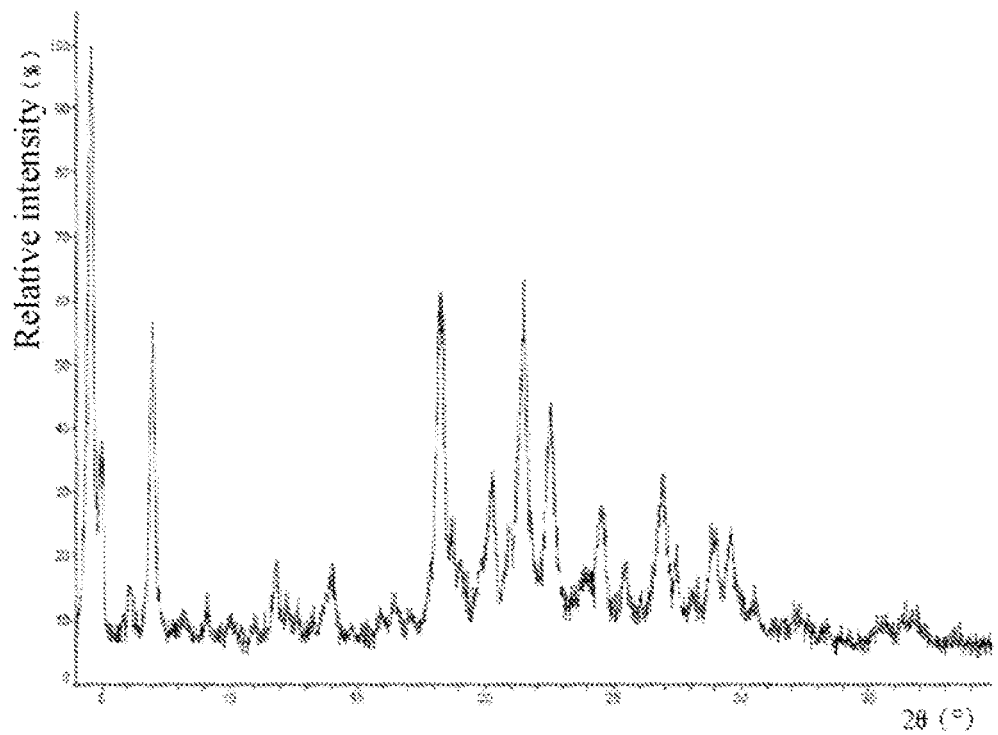
FIG. 17 is an XRPD pattern of the crystal form L of the compound of Formula (IV) obtained using Cu-Kα radiation.
Figure 18:
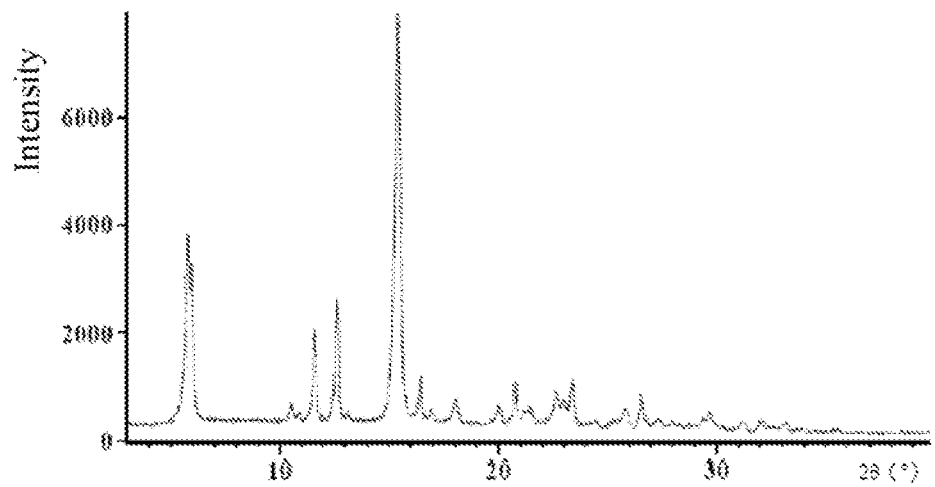
FIG. 18 is an XRPD pattern of the crystal form M of a compound of Formula (I) obtained using Cu-Kα radiation.
Figure 19:
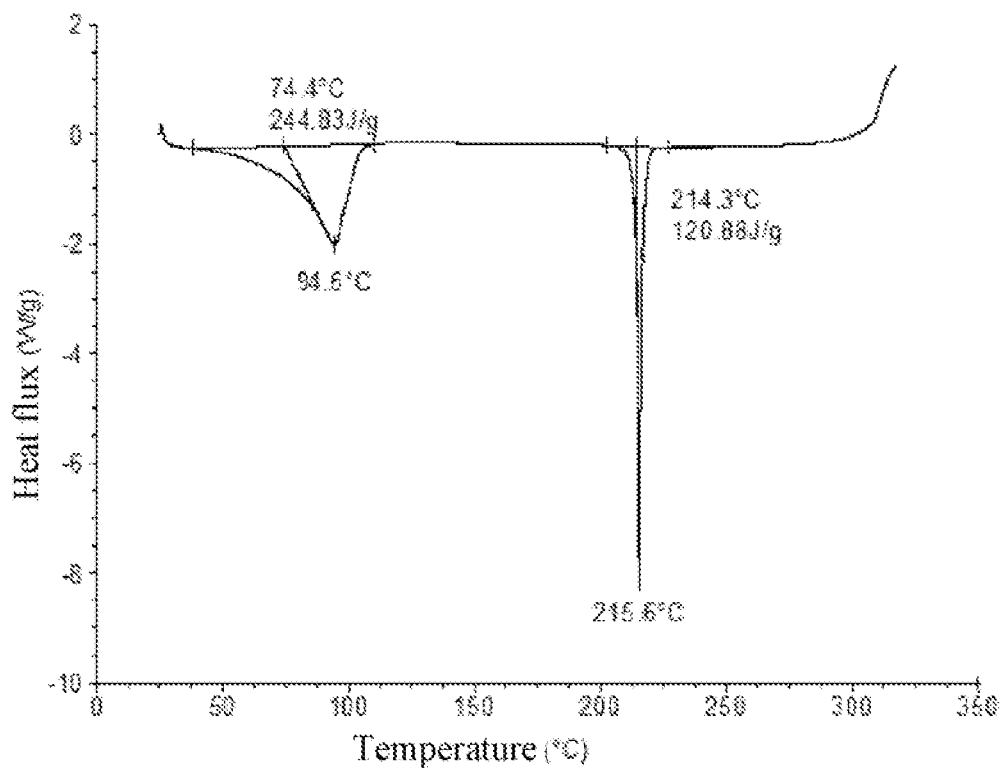
FIG. 19 is a DSC profile of the crystal form M of the compound of Formula (I).
Figure 20:
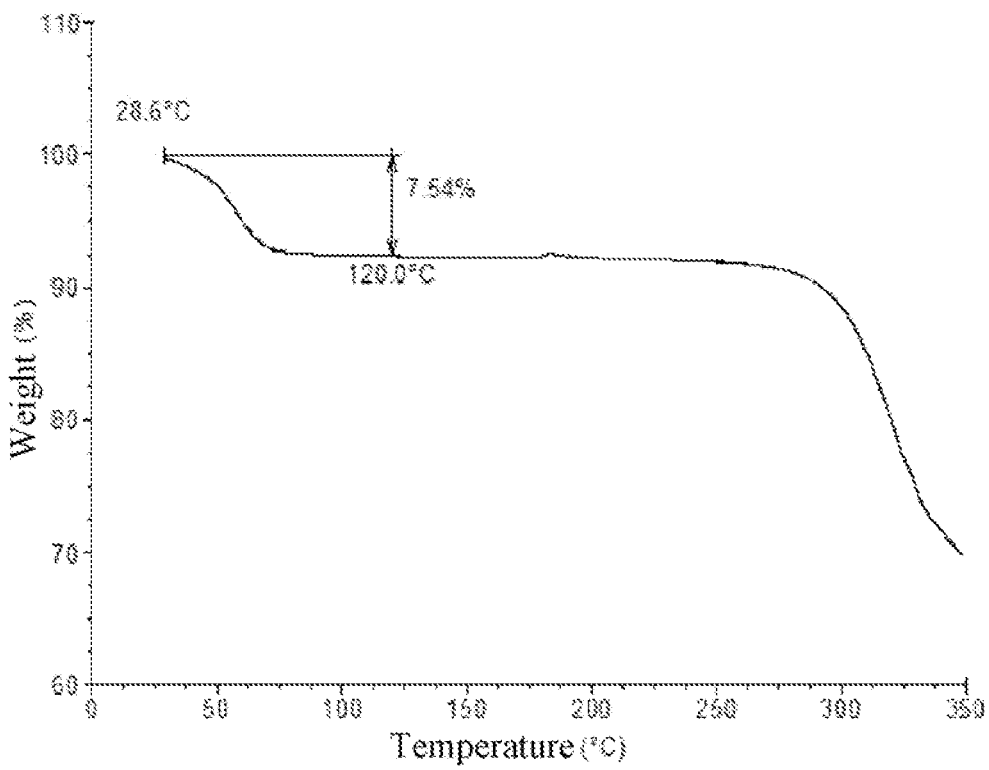
FIG. 20 is a TGA curve of the crystal form M of the compound of Formula (I).
Figure 21:
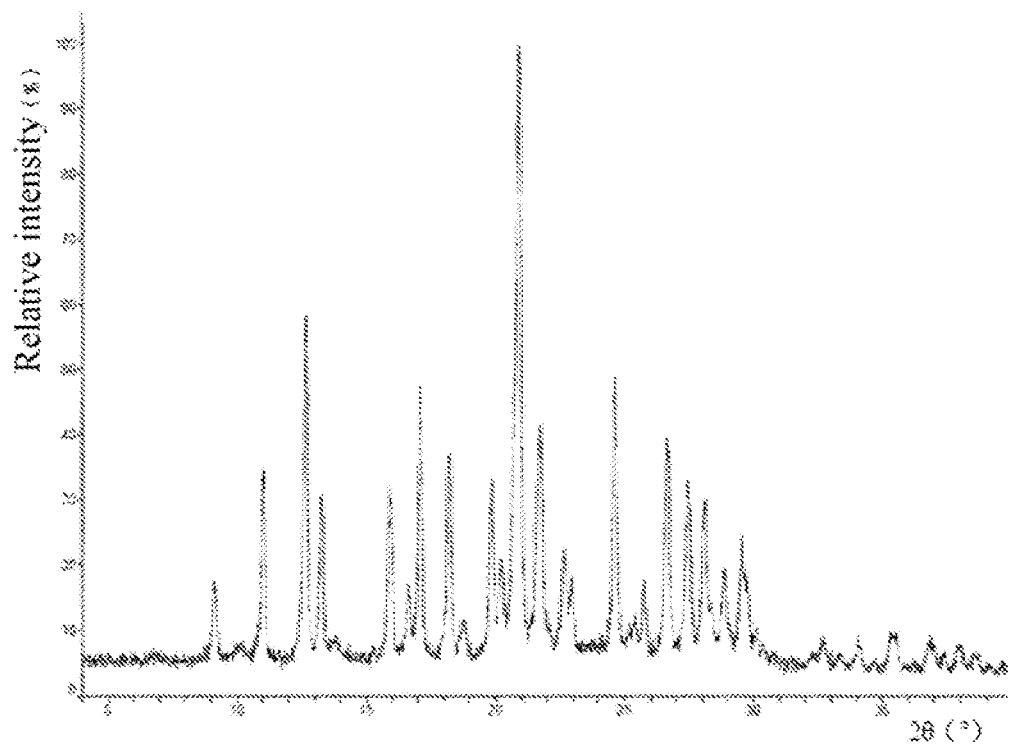
FIG. 21 is an XRPD pattern of the crystal form N of the compound of Formula (I) obtained using Cu-Kα radiation.
Figure 22:
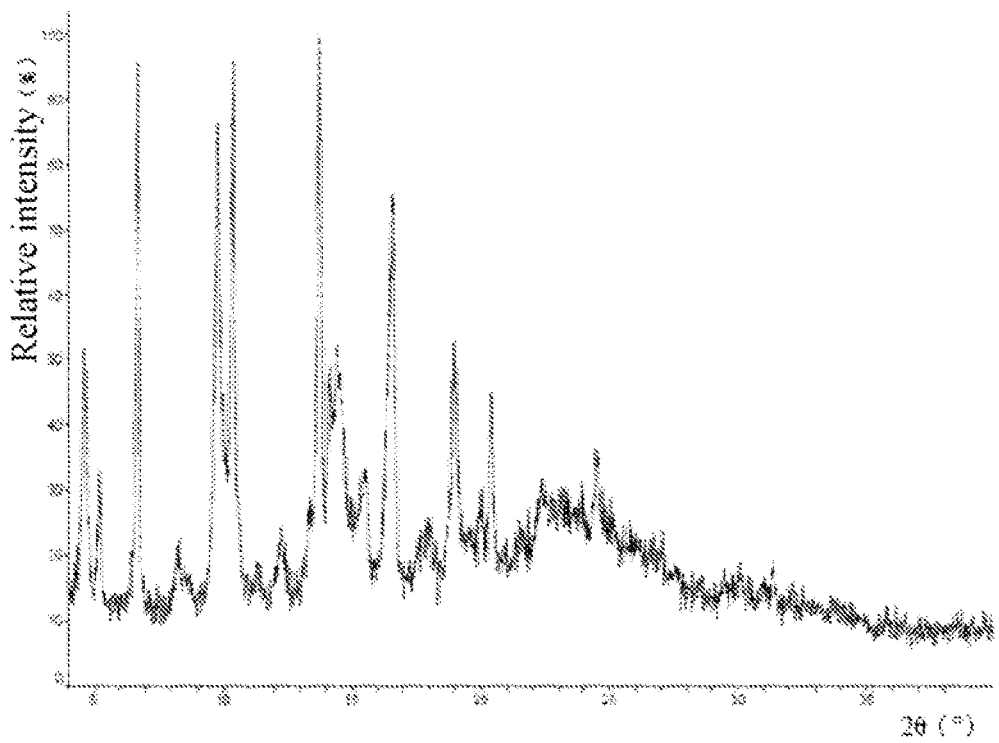
FIG. 22 is an XRPD pattern of the crystal form O of the compound of Formula (I) obtained using Cu-Kα radiation.

For better understanding of the present invention, the present invention will be further described in conjunction with specific embodiments; however, these specific embodiments are not intended to limit the disclosure of the present invention.

Example 1: Preparation of Crystal Form A of Compound of Formula (II)

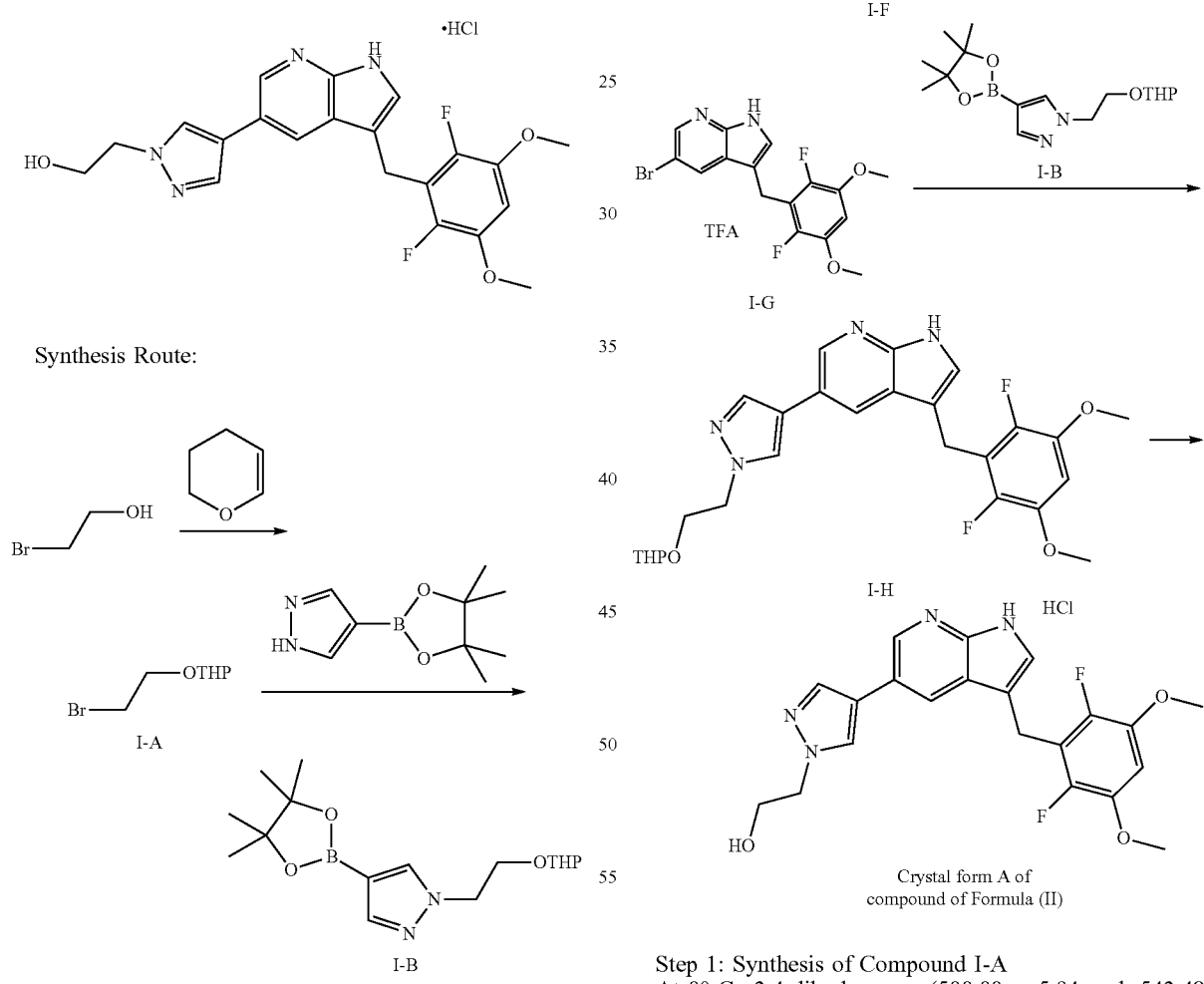

Step 1: Synthesis of Compound I-A

At 0° C., 3,4-dihydropyran (500.00 g, 5.94 mol, 543.48 mL) and concentrated hydrochloric acid (1.02 g, 10.35 mmol, 1.00 mL) were added to bromoethanol (500 g, 4.00 mol, 284.09 mL), and stirred at 19° C. for 1 hr. After the reaction was completed, 100 g of sodium bicarbonate was added and stirred for 30 min. The insolubles were removed by filtration to obtain a crude product. The filtrate was distilled under reduced pressure of 0.09 MPa, and the fraction at 80° C. was collected to obtain Compound I-A.

$^1$H NMR (400 MHz, CDCl$_3$) δ 4.66-4.60 (m, 1H), 4.00-3.76 (m, 3H), 3.50-3.47 (m, 1H), 1.83-1.50 (m, 6H).

Step 2: Synthesis of Compound I-B

Compound I-A (600.78 g, 2.87 mol, 435.35 mL) and 4-boronate-1H-pyrazole (280 g, 1.44 mol) were dissolved in N,N-dimethylformamide (1120 mL), and then potassium carbonate (397.12 g, 2.87 mol) was added, and stirred at 60° C. for 48 hrs. TLC showed that the starting materials were reacted completely. The insolubles were removed by filtration, the filter cake was washed with ethyl acetate, the filtrates were combined, and the solvent was spun off to obtain the crude product. The crude product was purified by column chromatography on silica gel (heptane:ethyl acetate=8:1) to obtain Compound 1-B.

$^1$H NMR (400 MHz, CDCl$_3$) δ 7.84-7.78 (m, 1H), 4.52-4.51 (m, 1H), 4.35-4.32 (m, 2H), 4.05-4.04 (m, 1H), 3.79-3.45 (m, 3H), 1.79-1.47 (m, 6H), 1.32 (s, 12H).

Step 3: Synthesis of Compound I-D

Compound I-C (250 g, 1.50 mol) and 1-chloromethyl-4-fluoro-1,4-diazabicyclo[2.2.2]octane bis(tetrafluoroborate) (1.33 kg, 3.76 mol) were added to acetonitrile (3750 mL), and reacted at 20-30° C. for 48 hrs. 19 L of water was slowly added to the reaction solution, and the reaction solution was filtered. The filter cake was washed with water (50 mL*2) to obtain a crude product. The crude product was purified by column chromatography (PE/DCM/EA=3/1/0-3/1/0.2). The obtained product (470 g) was added to n-heptane (2 L), and stirred at 10-20° C. for 30 min. The reaction system was stirred until uniform. After filtration, the filter cake was washed with n-heptane (50 mL) to obtain Compound I-D.

$^1$H HNMR (400 MHz, CDCl$_3$) δ 10.34-10.18 (m, 1H), 6.90-6.73 (m, 1H), 3.84 (s, 6H).

Step 4: Synthesis of Compound I-F

Compound I-D (460 g, 2.28 mol) and Compound I-E (407.58 g, 2.07 mol) were added to methanol (1.8 L), and the reaction was heated to 40° C. A solution of potassium hydroxide (232.12 g, 4.14 mol) in methanol was added dropwise to the reaction flask, and the reaction was stirred at 40° C. for 10 min. The reaction temperature was lowered to 10 to 20° C. when the reaction solution was clear, and the reaction was stirred at this temperature for 16 hrs. The reaction solution was filtered under reduced pressure. The filter cake was washed with methanol (50 mL), and spin-dried under reduced pressure at 40-50° C. to obtain Compound I-F.

LCMS (ESI) m/z: 398.6 [M+1]$^+$, 400.6 [M+1]$^+$;

$^1$H NMR (400 MHz, CDCl$_3$) δ 8.24 (s, 1H), 8.00 (s, 1H), 7.30 (s, 1H), 6.94 (t, J=8.0 Hz, 1H), 3.84 (s, 6H).

Step 5: Synthesis of Compound I-G 2.90 L of acetonitrile was added to a 5 L reaction flask at 10-25° C. Compound I-F (290.00 g) was added to the reaction flask in one portion with stirring at 10° C.-25° C., and then triethylsilane (232 mL) and trifluoroacetic acid (161 mL) were sequentially added dropwise to the reaction flask at 10° C.-25° C. The reaction was heated to an internal temperature of 55° C.-60° C., and the reaction was continuously stirred for 4 hrs at this temperature range. The reaction solution was cooled to room temperature (10-25° C.) and left to stand overnight. The reaction was filtered under reduced pressure, and the filter cake was rinsed with acetonitrile (100 mL*2). The filter cake was concentrated at a temperature of 40-50° C. under reduced pressure at a vacuum level of ≤0.08 MPa by using an oil pump until no fractions were dropped, to obtain Compound I-G.

LCMS (ESI) m/z: 382.6 [M+1]$^+$, 384.6 [M+1]$^+$;

$^1$H NMR (400 MHz, DMSO-d$_6$) δ 11.75 (s, 1H), 8.25 (s, 1H), 8.09 (s, 1H), 7.25 (s, 1H), 6.88 (t, J=8.0 Hz, 1H), 4.02 (s, 2H), 3.84 (s, 6H).

Step 6: Synthesis of Compound I-H 2.6 L of tetrahydrofuran and 0.52 L of distilled water were added into a 5 L reaction flask at 10-25° C. The content in the reaction flask was stirred and purged three times with nitrogen. Then, under nitrogen atmosphere, potassium carbonate (105.51 g) was added into the reaction flask. Compound I-G (130.00 g), Compound I-B (100.91 g) and Pd(dppf)Cl$_2$ (5.64 g) were added to the reaction flask under nitrogen atmosphere at 10° C.-25° C. The reaction was heated to an internal temperature of 65° C.-70° C., and the reaction was continuously stirred for 8-10 hrs at this temperature range. The reaction solution was cooled to room temperature (10-25° C.). Trithiocyanuric acid trisodium salt (130.00 g) was added in one portion, and stirred at 10° C.-25° C. for 16-20 hrs. The reaction solution was filtered through 200-300 g of diatomaceous earth, and then the filter cake was rinsed with tetrahydrofuran (120 mL*2). Trithiocyanuric acid trisodium salt (130.00 g) was added to the filtrate in one portion, and stirred at 10° C.-25° C. for 16-20 hrs. The reaction solution was filtered through 200-300 g of diatomaceous earth, and then the filter cake was rinsed with tetrahydrofuran (120 mL*2). 1.2 L of purified water was added to the filtrate, and the reaction solution was extracted with ethyl acetate (3.6 L*2). The combined organic phases were washed with saturated sodium chloride (1.2 L*2), and dried over anhydrous sodium sulfate (500 g) for 1-2 hrs. After filtration, the filtrate was concentrated under reduced pressure until no fractions were dropped to obtain a primary crude product. The primary crude product was purified by column chromatography to obtain a crude product. The crude product was dissolved in 1.6 L of ethyl acetate, heated to 45° C.-50° C., and cooled to 10° C.-25° C. after complete dissolution. 4.8 L of n-heptane was added dropwise over 0.5-1 hr with stirring. After a solid was precipitated, the reaction solution was continuously stirred at 10° C.-25° C. for 1 hr and filtered. The filter cake was washed with n-heptane (250 mL*2). The filter cake was concentrated under reduced pressure by using an oil pump until no fractions was dropped to obtain a crude product. The crude product was dissolved in 1.6 L of tetrahydrofuran at 10° C.-25° C., then about 250 g of a polymer resin PSB-22Y was added, heated to 55° C.-60° C., and stirred for 16-20 hrs at this temperature (300-305 r/mm). The liquid was filtered through 200-300 g of diatomaceous earth, and then rinsed with tetrahydrofuran (150 mL*2). Then about 250 g of PSB-22Y was added to the filtrate, heated to 55° C.-60° C., and stirred for 16-20 hrs (at a rotation speed of 300-305 r/mm). The liquid was filtered through 200-300 g of diatomaceous earth, and then rinsed with tetrahydrofuran (150 mL*2). The filtrate was concentrated under reduced pressure by a water pump until no fraction was dropped, wherein the temperature was 40° C.-50° C., and the vacuum level was ≤0.08 MPa to obtain Compound I-H.

LCMS (ESI) m/z: 499.5 [M+1]$^+$;

$^1$H NMR (400 MHz, DMSO-d$_6$) δ 11.75 (s, 1H), 8.45 (s, 1H), 8.15 (s, 1H), 8.05 (s, 1H), 7.87 (s, 1H), 7.12 (s, 1H), 6.88 (t, J=8.0 Hz, 1H), 4.57 (s, 1H), 4.38-4.32 (m, 2H), 4.06 (s, 2H), 3.97-3.92 (m, 1H), 3.84 (s, 6H), 3.79-3.78 (m, 1H), 3.58-3.37 (m, 2H), 1.76-1.36 (m, 6H).

Step 7: Synthesis of Crystal Form A of Compound of Formula (II)

2.78 L of ethanol was added to a 5 L three-neck flask at 25° C. 25° C. After heating to 20-30° C., Compound I-H (139.00 g) was added with stirring, and the suspension was stirred at 20-30° C. for about 30 min. Hydrochloric acid/ethyl acetate (137 mL, 4M) was added dropwise at 20-30° C. over 20 min. The reaction was mechanically stirred for 16-20 hrs at 20-30° C. Then the reaction solution was cooled to 10-25° C. and filtered under reduced pressure. The filter cake was rinsed with ethanol (200 mL*2). The filter cake was concentrated under reduced pressure until no fraction was dropped, wherein the temperature was 40-50° C., and the vacuum level was ≤−0.08 MPa to obtain the crystal form A of the compound of Formula (II).

LCMS (ESI) m/z: 415.0 [M+1]$^+$;

$^1$H NMR (400 MHz, DMSO-d$_6$) δ 11.98 (s, 1H), 8.58 (s, 1H), 8.40 (s, 1H), 8.24 (s, 1H), 7.96 (s, 1H), 7.19 (s, 1H), 6.88 (t, J=8.0 Hz, 1H), 4.57 (s, 1H), 4.25-4.10 (m, 4H), 3.85 (s, 6H), 3.84-3.80 (m, 2H).

Study of Salt Forming Number

From the molecular formula $C_{21}H_{20}F_2N_4O_3HCl$, the theoretical content of Cl ions was calculated to be 7.87%, which is very close to 7.04%. Therefore, the salt forming number of the compound of Formula (I) as a hydrochloride is 1.

|   | Sample weight (mg) | Test item | Weight percent (w/w %) |
|---|---|---|---|
| 1 | 41.7 | Cl | 7.1481 |
| 3 | 40.96 | Cl | 6.9307 |
|   | Average | Cl1 | 7.04 |

Example 2

Preparation of Crystal Form M of Compound of Formula (I)

50 mg of the crystal form A of the compound of Formula (II) was weighed, dissolved in water, dissociated with a saturated aqueous sodium bicarbonate solution, and stirred at 15° C. for 1 hr. The reaction solution was filtered, and the filter cake was subjected to rotary evaporation to dryness under reduced pressure, to obtain the crystal form M of the compound of Formula (I).

Preparation of Crystal Form a of Compound of Formula (II)

100 mg of the crystal form M of the compound of Formula (I) was weighed into a glass vial, 4.0 mL of ethanol was added, then hydrogen chloride/ethyl acetate (4 M, 60 μL) was slowly added, and the reaction solution was stirred at 15° C. for 48 hrs. The reaction solution was filtered, and the filter cake was dried under reduced pressure (40° C.), to obtain the crystal form A of the compound of Formula (II).

350 mg of the crystal form M of the compound of Formula (I) was weighed into a glass vial, 10 mL of methanol was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.) to obtain the crystal form A of the compound of Formula (II).

Preparation of Crystal Form B of Compound of Formula (II)

100 mg of the crystal form M of the compound of Formula (I) was weighed into a glass vial, 4.0 mL of acetone was added, then hydrogen chloride/ethyl acetate (4 M, 60 μL) was slowly added, and the reaction solution was stirred at 15° C. for 48 hrs. The reaction solution was filtered, and the filter cake was dried under reduced pressure (40° C.), to obtain the crystal form B of the compound of Formula (II).

Preparation of Crystal Form C of Compound of Formula (II)

50 mg of the crystal form M of the compound of Formula (I) was weighed into a glass vial, 4.0 mL of ethyl acetate was added, then hydrogen chloride/ethyl acetate (4 M, 30 μL) was slowly added, and the reaction solution was stirred at 15° C. for 48 hrs. The reaction solution was filtered, and the filter cake was dried under reduced pressure (40° C.), to obtain the crystal form C of the compound of Formula (II).

Preparation of Crystal Form D of Compound of Formula (II)

350 mg of the crystal form M of the compound of Formula (I) was weighed into a glass vial, 10 mL of acetone was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.) to obtain the crystal form D of the compound of Formula (II).

350 mg of the crystal form M of the compound of Formula (I) was weighed into a glass vial, 10 mL of ethyl acetate was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.), to obtain the crystal form D of the compound of Formula (II).

350 mg of the crystal form M of the compound of Formula (I) was weighed into a glass vial, 10 mL of tetrahydrofuran was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.), to obtain the crystal form D of the compound of Formula (II).

350 mg of the crystal form M of the compound of Formula (I) was weighed into a glass vial, 10 mL of acetone/water (v/v, 1/1) was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.), to obtain the crystal form D of the compound of Formula (II).

Preparation of Crystal Form E of Compound of Formula (II)

350 mg of the crystal form M of the compound of Formula (I) was weighed into a glass vial, 10 mL of tetrahydrofuran/water (v/v, 1/1) was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.), to obtain the crystal form E of the compound of Formula (II).

Preparation of Crystal Form F of Compound of Formula (II)

350 mg of the crystal form M of the compound of Formula (I) was weighed into a glass vial, 10 mL of ethanol/water (v/v, 1/1) was added, and then 0.21 mL of hydrogen chloride/ethyl acetate (4 M) was slowly added to obtain a suspension. The suspension was stirred on a magnetic stirrer at 15° C. for 24 hrs (in the dark). The reaction solution was filtered, and the filter cake was dried in a vacuum drying oven (40° C.), to obtain the crystal form F of the compound of Formula (II).

Preparation of Crystal Form G of Compound of Formula (III)

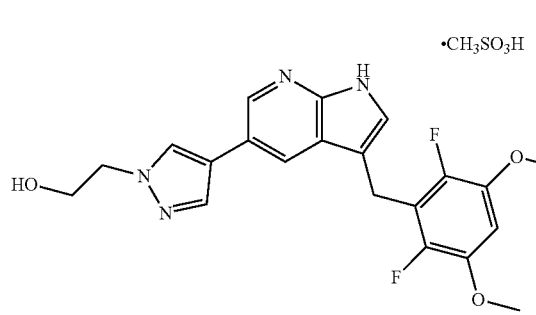

(III)
·CH$_3$SO$_3$H 100 mg of the crystal form M of the compound of Formula (I) was weighed into a glass vial, 4.0 mL of ethanol was added, then methanesulfonic acid (26 mg, 1.1 eq) was slowly added, and the reaction solution was stirred at 15° C. for 48 hrs. The reaction solution was filtered, and the filter cake was dried under reduced pressure (40° C.), to obtain the crystal form G of the compound of Formula (III).

$^1$H NMR (400 MHz, DMSO-d$_6$) δ 11.66 (s, 1H), 8.51 (s, 1H), 8.20 (s, 2H), 7.90 (s, 1H), 7.15 (s, 1H), 6.90 (t, J=8.0 Hz, 1H), 4.08-4.21 (m, 4H), 3.84 (s, 6H), 3.76-3.78 (m, 2H), 2.33 (s, 3H).

Preparation of Crystal Form H of Compound of Formula (III)

100 mg of the crystal form M of the compound of Formula (I) was weighed into a glass vial, 4.0 mL of acetone was added, then methanesulfonic acid (26 mg, 1.1 eq) was slowly added, and the reaction solution was stirred at 15° C. for 48 hrs. The reaction solution was filtered, and the filter cake was dried under reduced pressure (40° C.), to obtain the crystal form H of the compound of Formula (III).

Preparation of Crystal Form I of Compound of Formula (III)

50 mg of the crystal form M of the compound of Formula (I) was weighed into a glass vial, 4.0 mL of ethyl acetate was added, then methanesulfonic acid (13 mg, 1.1 eq) was slowly added, and the reaction solution was stirred at 15° C. for 48 hrs. The reaction solution was filtered, and the filter cake was dried under reduced pressure (40° C.), to obtain the crystal form I of the compound of Formula (III).

Preparation of Crystal Form J of Compound of Formula (IV)

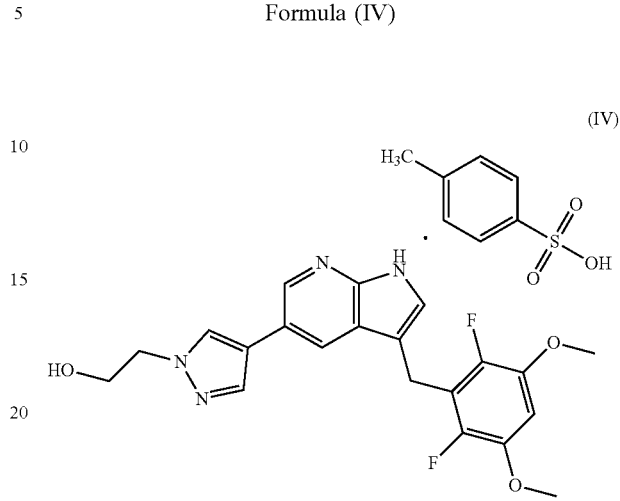

(IV)

100 mg of the crystal form M of the compound of Formula (I) was weighed into a glass vial, 4.0 mL of ethanol was added, then p-toluenesulfonic acid (50 mg, 1.1 eq) was slowly added, and the reaction solution was stirred at 15° C. for 48 hrs. The reaction solution was filtered, and the filter cake was dried under reduced pressure (40° C.), to obtain the crystal form J of the compound of Formula (IV).

$^1$H NMR (400 MHz, DMSO-d$_6$) δ 11.91 (s, 1H), 8.57 (s, 1H), 8.40 (s, 1H), 8.24 (s, 1H), 7.95 (s, 1H), 7.49-7.47 (m, 2H), 7.21 (s, 1H), 7.13-7.11 (m, 1H), 6.90 (t, J=8.0 Hz, 1H), 4.22-4.11 (m, 4H), 3.85 (s, 6H), 3.81-3.78 (m, 2H), 2.29 (s, 3H).

Preparation of Crystal Form K of Compound of Formula (IV)

100 mg of the crystal form M of the compound of Formula (I) was weighed into a glass vial, 4.0 mL of acetone was added, then p-toluenesulfonic acid (50 mg, 1.1 eq.) was slowly added, and the reaction solution was stirred at 15° C. for 48 hrs. The reaction solution was filtered, and the filter cake was dried under reduced pressure (40° C.), to obtain the crystal form K of the compound of Formula (IV).

Preparation of Crystal Form L of Compound of Formula (IV)

50 mg of the crystal form M of the compound of Formula (I) was weighed into a glass vial, 4.0 mL of ethyl acetate was added, then p-toluenesulfonic acid (25 mg, 1.1 eq.) was slowly added, and the reaction solution was stirred at 15° C. for 48 hrs. The reaction solution was filtered, and the filter cake was dried under reduced pressure (40° C.), to obtain the crystal form L of the compound of Formula (IV).

Preparation of Crystal Form N of Compound of Formula (I)

50 mg of the crystal form M of the compound of Formula (I) was weighed into a glass vial, and 2.0 mL of acetone was added to obtain a suspension. The suspension was stirred on a magnetic stirrer (15° C.) for 16 hrs. The reaction solution was filtered, and the filter cake was dried under reduced pressure (40° C.), to obtain the crystal form N of the compound of Formula (I).

50 mg of the crystal form M of the compound of Formula (I) was weighed into a glass vial, and 2.0 mL of tetrahydrofuran was added to obtain a suspension. The suspension was stirred on a magnetic stirrer (15° C.) for 16 hrs. The reaction solution was filtered, and the filter cake was dried under reduced pressure (40° C.), to obtain the crystal form N of the compound of Formula (I).

50 mg of the crystal form M of the compound of Formula (I) was weighed into a glass vial, and 2.0 mL of ethanol was added to obtain a suspension. The suspension was stirred on a magnetic stirrer (15° C.) for 16 hrs. The reaction solution was filtered, and the filter cake was dried under reduced pressure (40° C.), to obtain the crystal form N of the compound of Formula (I).

50 mg of the crystal form M of the compound of Formula (I) was weighed into a glass vial, and 2.0 mL of ethyl acetate was added to obtain a suspension. The suspension was stirred on a magnetic stirrer (15° C.) for 16 hrs. The reaction solution was filtered, and the filter cake was dried under reduced pressure (40° C.), to obtain the crystal form N of the compound of Formula (I).

50 mg of the crystal form M of the compound of Formula (I) was weighed into a glass vial, and 2.0 mL of ethanol/water (v/v, 1/1) was added to obtain a suspension. The suspension was stirred on a magnetic stirrer (15° C.) for 16 hrs. The reaction solution was filtered, and the filter cake was dried under reduced pressure (40° C.), to obtain the crystal form N of the compound of Formula (I).

50 mg of the crystal form M of the compound of Formula (I) was weighed into a glass vial, and 2.0 mL of acetone/water (v/v, 1/1) was added to obtain a suspension. The suspension was stirred on a magnetic stirrer (15° C.) for 16 hrs. The reaction solution was filtered, and the filter cake was dried under reduced pressure (40° C.), to obtain the crystal form N of the compound of Formula (I).

Preparation of Crystal Form O of Compound of Formula (I)

50 mg of the crystal form M of the compound of Formula (I) was weighed into a glass vial, and 2.0 mL of tetrahydrofuran/water (v/v, 1/1) was added to obtain a suspension. The suspension was stirred on a magnetic stirrer (15° C.) for 16 hrs. The reaction solution was filtered, and the filter cake was dried under reduced pressure (40° C.), to obtain the crystal form O of the compound of Formula (I).

Example 3

Figure 23:
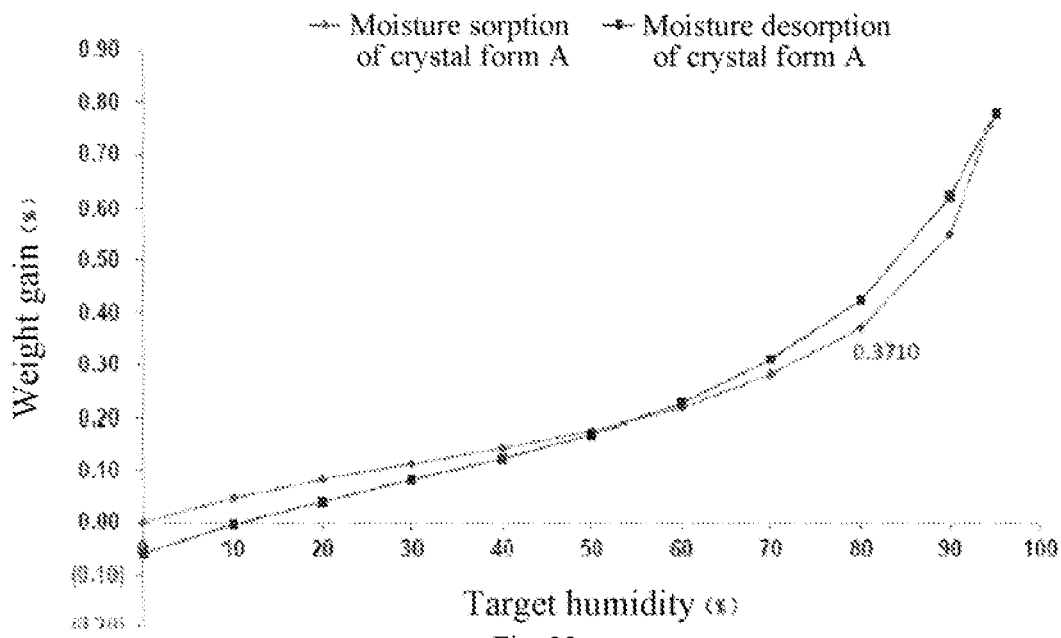
FIG. 23 is a DVS curve of the crystal form A of the compound of Formula (II).

Hygroscopicity Test of Crystal Form A of Compound of Formula (II)
  Experimental Materials:
  SMS DVS Intrinsic Dynamic Vapor Sorption Analyzer
  Experimental Method:
  10-30 mg of the crystal form A of the compound of Formula (II) was placed in the DVS sample pan and tested.
  Experimental Results
  The crystal form A of the compound of Formula (II) has a DVS curve as shown in FIG. 23, wherein $\Delta W=0.3710\%$.
  Experimental Conclusions
  The crystal form A of the compound of Formula (II) has a hygroscopic weight gain of 0.3710% at 25° C. and 80% RH, and is slightly hygroscopic.

Figure 24:
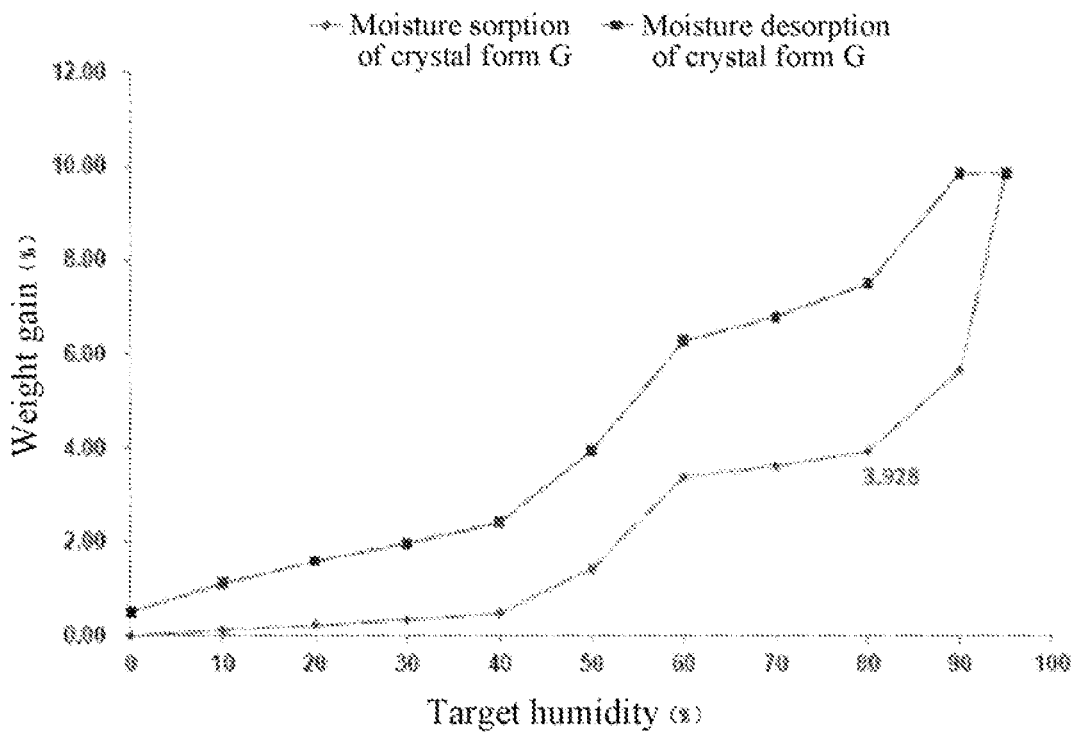
FIG. 24 is a DVS curve of the crystal form G of the compound of Formula (III).

Hygroscopicity Test of Crystal Form G of Compound of Formula (III)
  Experimental Materials:
  SMS DVS Intrinsic Dynamic Vapor Sorption Analyzer
  Experimental Method:
  10-30 mg of the crystal form G of the compound of Formula (III) was placed in the DVS sample pan and tested.
  Experimental Results
  The crystal form G of the compound of Formula (III) has a DVS curve as shown in FIG. 24, wherein $\Delta W=3.829\%$.
  Experimental Conclusions
  The crystal form G of the compound of Formula (III) has a hygroscopic weight gain of 3.928% at 25° C. and 80% RH, and is hygroscopic.

Figure 25:
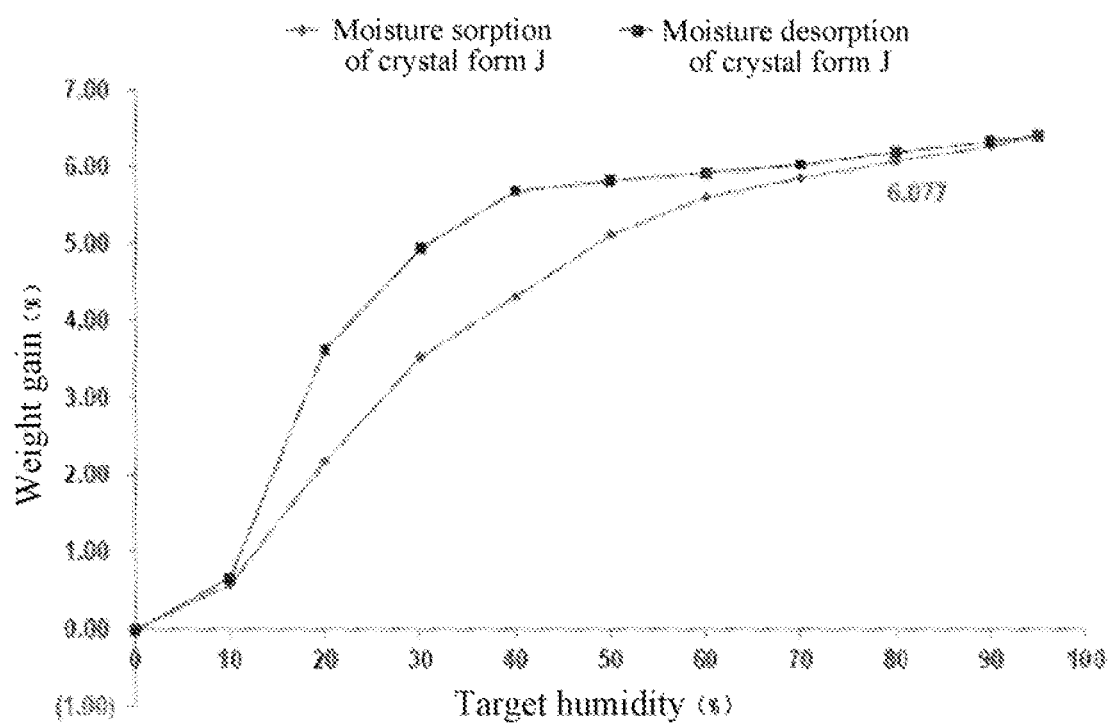
FIG. 25 is a DVS curve of the crystal form J of the compound of Formula (II).

Hygroscopicity Test of Crystal Form J of Compound of Formula (IV)
  Experimental Materials:
  SMS DVS Intrinsic Dynamic Vapor Sorption Analyzer
  Experimental Method:
  10-30 mg of the crystal form J of the compound of Formula (IV) was placed in the DVS sample pan and tested.
  Experimental Results
  The crystal form J of the compound of Formula (IV) has a DVS curve as shown in FIG. 25, wherein $\Delta W=6.077\%$.
  Experimental Conclusions
  The crystal form J of the compound of Formula (IV) has a hygroscopic weight gain of 6.077% at 25° C. and 80% RH, and is hygroscopic.

To Sum Up: DVS Data Shows that Hydrochloride is the Least Hygroscopic.

Example 4: Solubility Test of Crystal Form A of Compound of Formula (II) at Various pH The solubility of the crystal form A of the compound of Formula (II) in 4 media with different pH values was tested. About 10 mg of the crystal form A of the compound of Formula (II) was weighed, and then 5.0 mL of different media (water, SGF, FaSSIF, and FeSSIF) were added respectively, to form a suspension. A magnetron was added to the suspension and the suspension was stirred on a magnetic stirrer for 2 hrs, and a sample was taken and centrifuged after 4 hrs. The sample in the upper layer was determined for concentration by HPLC and determined for the pH value. The test results are shown in Table 16:

TABLE 16

Solubility test results of crystal form A of compound of Formula (II) at various pH

|  | pH (24 h) | State (24 h) | Solubility (mg/ml)_24 h |
| --- | --- | --- | --- |
| Water | 2.42 | Suspension | 0.009 |
| SGF | 1.25 | Suspension | 0.112 |
| FeSSIF | 4.89 | Suspension | 0.252 |
| FaSSIF | 5.55 | Suspension | 0.004 |

FaSSIF: (1). 0.042 g of sodium hydroxide, 0.3438 g of sodium dihydrogen phosphate and 0.6186 g of sodium chloride were weighed, added to 90 mL of purified water and mixed well. The solution was adjusted to pH 6.5 with 1 N hydrochloric acid or 1 N sodium hydroxide, and made up to 100 mL with purified water. (2). 0.224 g of commercially available powder of FaSSIF/FeSSIF/FaSSGF was added to 50 mL of the buffer, stirred until dissolved, and made up to 100 mL with purified water. The prepared buffer was left to stand at room temperature for 2 hrs, and observed to be slightly milky white, which was ready for use (simulating intestinal juice in human before eating).

FeSSIF: (1). 0.404 g of sodium hydroxide, and 0.865 g of glacial acetic acid, 1.1874 g of sodium chloride were weighed and added to 90 mL of purified water and mixed well. The solution was adjusted to pH 5.0 with 1 N hydrochloric acid or 1 N sodium hydroxide, and made up to 100 mL with purified water. (2). 1.12 g of commercially available powder of FaSSIF/FeSSIF/FaSSGF was added to 50 mL of the buffer, stirred until dissolved, and made up to 100 mL with purified water. The prepared buffer was left to stand at room temperature for 2 hrs, and observed to be a clear liquid, which was ready for use (simulating intestinal juice in human after eating).

FaSSGF (SGF): (1). 0.2 g of sodium chloride was weighed and added to 90 mL of purified water and mixed well. The solution was adjusted to pH 1.8 with 1 N hydrochloric acid, made up to 100 mL with purified water, and left to stand until it was naturally cooled to room temperature (simulating human gastric juice before eating).

Conclusions: The solubility data of the crystal form A of the compound of Formula (II) in biological media shows that it is hard to dissolve in water; the solubility in the simulated intestinal juice of the small intestine after eating in human and the simulated gastric juice before eating in human is good; and the solubility in the simulated intestinal juice before eating is poor.

Example 5: Solid Stability Test of Crystal Form A of Compound of Formula (II)

Experimental method: 12 parallel samples of the crystal form A of the compound of formula (II) were weighed in an amount of about 1 g each. Each sample was fed to a double-layer LDPE bag, and each layer of the LDPE bag was tied and sealed. Then the LDPE bag was placed in a bag of aluminum foil, and allowed to stand at 60° C./75% RH, 92.5% RH, and 40° C./75% RH to investigate the long-term accelerated stability. The photostability experiment was carried out as described in the Chinese Pharmacopoeia and ICH Q1B. The samples were irradiated with visible light and UV light.

The test results are shown in Table 17 below:

TABLE 17

Solid stability test results of crystal form A of compound of Formula (II)

| Test conditions | Time point | Appearance | Crystal form (XRPD) | Content (%) | Total impurity (%) |
|---|---|---|---|---|---|
| — | Day 0 | Off-white particles and powder | Crystal form A | 99.8 | 0.71 |

TABLE 17-continued

Solid stability test results of crystal form A of compound of Formula (II)

| Test conditions | Time point | Appearance | Crystal form (XRPD) | Content (%) | Total impurity (%) |
|---|---|---|---|---|---|
| High temperature. (60° C., open) | Day 5 | Off-white particles and powder | Crystal form A | 99.6 | 0.78 |
| | Day 10 | Off-white particles and powder | Crystal form A | 99.9 | 0.76 |
| | Day 30 | Off-white particles and powder | Crystal form A | 98.5 | 0.80 |
| High humidity (Room temperature/ relative humidity 92.5%, open) | Day 5 | Off-white particles and powder | Crystal form A | 99.6 | 0.75 |
| | Day 10 | Off-white particles and powder | Crystal form A | 99.8 | 0.71 |
| | Day 30 | Off-white particles and powder | Crystal form A | 98.9 | 0.65 |
| Light irradiation (General lighting: 1.2 × 10$^6$Lux · hr/ near ultraviolet: 200 w · hr/m$^2$, open 10 days) | Light irradiation | Off-white particles and powder | Crystal form A | 99.8 | 0.76 |
| | In the dark | Off-white particles and powder | Crystal form A | 99.8 | 079 |
| Acceleration experiment (40° C./relative humidty 75%, open) | 1 month | Off-white particles and powder | Crystal form A | 99.7 | 0.67 |
| | 2 month | Off-white particles and powder | Crystal form A | 99.7 | 0.69 |
| | 3 month | Off-white particles and powder | Crystal form A | 99.9 | 0.68 |

Conclusions: With the accelerated conditions and affecting factors, the crystal form A of the compound of Formula (II) is very stable, and no obvious unknown impurities are formed.

Example 6: Stability Test of Crystal Form A and Crystal Form B of Compound of Formula (II)

35 g of the crystal form B of the compound of Formula (II) was weighed, added to ethanol, and stirred for 16 hrs. XRPD shows that the crystal form B of the compound of Formula (II) can be converted into the crystal form A of the compound of Formula (II). Therefore, the crystal form A of the compound of Formula (II) is more stable than the crystal form B of the compound of Formula (II).

Test Example 1: In-Vitro Enzyme Activity Assay of the Compounds of the Present Invention The IC$_{50}$ value was tested by $^{33}$P isotope-labeled kinase activity assay (Reaction Biology Corp) to evaluate the inhibition of the test compounds on human FGFR1, FGFR4, and c-Met.

Buffer: 20 mM Hepes (pH 7.5), 10 mM MgCl$_2$, 1 mM EGTA, 0.02% Brij35, 0.02 mg/ml BSA, 0.1 mMNa$_3$VO$_4$, 2 mM DTT, and 1% DMSO.

Test procedure: At room temperature, the test compound was dissolved in DMSO to prepare a 10 mM solution for use. The substrate was dissolved in freshly prepared buffer, and the test kinase was added and mixed well. A solution of the test compound in DMSO was added to the mixed reaction solution using an acoustic technology (Echo550). The compound concentration in the reaction solution was 1 μM, 0.25 μM, 0.156 μM, 3.91 nM, 0.977 nM, 0.244 nM, 0.061 nM, 0.0153 nM, 0.00381 nM, or 10 μM, 2.50 μM, 0.62 μM, 0.156 μM, 39.1 nM, 9.8 nM, 2.4 nM, 0.61 nM, 0.15 nM, and 0.038 nM, respectively. After 15 min of incubation, $^{33}$P-ATP (with an activity of 0.01 μCi/nL, the corresponding concentration is listed in Table 18) was added to start the reaction. The supplier's catalogue number, lot number, and concentration in the reaction solution of FGFR1, FGFR4, c-Met, and substrates thereof are listed in Table 18. The reaction was carried out at room temperature for 120 min, and then the reaction solution was dotted on P81 ion-exchange filter paper (Whatman #3698-915). The filter paper was repeatedly washed with 0.75% phosphoric acid solution, and then the radioactivity of the phosphorylated substrate remaining on the filter paper was determined. The kinase activity data were expressed by the comparison of the kinase activity in the presence of the test compound with the kinase activity of the blank group (containing only DMSO), and an IC$_{50}$ value was obtained by curve fitting with Prism4 software (GraphPad). The test results are shown in Table 19.

TABLE 18

Relevant information of kinases, substrates and ATP in in-vitro assays.

| Kinase | Kinase concentration in the reaction solution (nM) | Substrate | Substrate concentration in the reaction solution (mg/ml) | ATP concentration (μM) |
|---|---|---|---|---|
| FGFR1 Supplier: Invitrogen Cat#: PV3146 Lot#: 28427Q | 1.75 | pEY(mg/ml) + Mn Supplier: Sigma Cat#: P7244-250MG Lot#: 062K5104V | 0.2 mg/mL | 5 |
| FGFR4 Supplier: Invitrogen Cat#: P3054 Lot#: 26967J | 2.5 | pEY(mg/ml) + Mn Supplier: Sigma Cat#: P7244-250MG Lot#: 062K5104V | 0.2 mg/mL | 100 |
| c-Met Supplier: Invitrogen Cat#: PV3143 Lot#: 464006A | 8 | MBP Supplier: Active Motif Cat#: 102641 Lot#: 04811001 | 20 μm | 10 |

TABLE 19

IC$_{50}$ values of the kinase in the examples

| Test sample | FGFR1 | FGFR4 | c-Met |
|---|---|---|---|
| Comparative Example 1a | 2419 | >10000 | 758.3 |
| Comparative Example 1b | 709.1 | 5092.0 | 11.1 |
| Crystal form A of compound of Formula (II) | 0.20 | 1.49 | 15.9 |

Note:
IC$_{50}$ is in nM.

Conclusions: Compared with the control, surprisingly, the crystal form A of the compound of Formula (II) has significantly improved activity against FGFR1 and FGFR4 and retains excellent activity against c-Met. The compounds of the present invention are obtained based on the structural analysis of the c-Met and FGFR kinase proteins, and a highly active small molecular nucleus that inhibits both c-Met and FGFR is found. The compounds of the present invention are an inhibitor against dual targets. The FGFR and c-Met targets are synergistic and complementary, and the FGFR mutation or c-Met mutation tend to have a signal compensation effect when the other is inhibited, thus making the tumor cells resistant to a single inhibitor. Such inhibitors against dual targets will potentially reduce tumor cell-dependent escape and greatly improve the effect of tumor treatment.

Test Example 2: Pharmacokinetic Evaluation of the Compounds of the Present Invention Experiment Procedure:

For agents for intravenous administration, 30% (v/v) PEG400 in purified water was as a vehicle. An appropriate amount of compound was accurately weighed into a glass flask, 30 vol % of PEG400 of the container volume was slowly added to the container with stirring, and then the remaining 70 vol % of pure water was added to make up to the final volume and stirred continuously until a clear solution was obtained. The solution was filtered through a 0.22 μM filter membrane, and stored at room temperature for later use. The agents for intravenous administration were formulated on the day of administration, and injected into male SD rats via tail vein (fasted overnight before administration) at a dose of 0.5 mg/kg. Approximately 0.18 mL of blood was collected from the jugular vein or tail vein at 0.0833, 0.25, 0.5, 1.0, 2.0, 4.0, 8.0 and 24 hrs after intravenous administration. The corresponding test compound in the vehicle was administered by gavage to male SD rats (fasted overnight before administration) at a dose of 5 mg/kg. The experimental conditions are detailed in Table 20. Blood was collected from the jugular or tail vein at 0.0833, 0.25, 0.5, 1.0, 2.0, 4.0, 6.0, 8.0 and 24 hrs after oral administration. The blood was fed to an anticoagulation tube supplemented with EDTA-K2, and centrifuged to separate plasma. The plasma concentrations were determined by LC-MS/MS, and the relevant pharmacokinetic parameters were calculated by the linear logarithmic trapezoid method of non-compartmental model using WinNonlm™ Version 6.3 (Pharsight, Mountain View, CA) pharmacokinetic software.

TABLE 20

Pharmacokinetic test conditions of compounds in rats

| | IV (injection) | | PO (oral administration) | |
|---|---|---|---|---|
| | Dose | Vehicle | Dose | Vehicle |
| Crystal form A of compound of Formula (II) | 0.5 mg/kg | 30% (v/v) PEG400 in purified water | 5 mg/kg | 1 mg/mL in 35% PEG400 + 65% water |
| Crystal form G of compound of Formula (III) | / | / | 5 mg/kg | 1 mg/mL in 35% PEG400 + 65% water |
| Crystal form J of compound of Formula (IV) | / | / | 5 mg/kg | 1 mg/mL in 35% PEG400 + 65% water |

TABLE 21

Pharmacokinetic test results of compounds in mice

| Parameter | IV Dose 0.5 mg/kg | | | | PO 5 mg/kg | | |
|---|---|---|---|---|---|---|---|
| | Cl (mL/min/kg) | Vdss (L/kg) | $T_{1/2}$ (h) | $AUC_{0-last}$ (nM·h) | $C_{max}$ (nM) | $T_{max}$ (h) | $AUC_{0-last}$ (nM·h) |
| Crystal form A of compound of Formula (II) | 18.4 | 1.87 | 1.32 | 1009 | 1960 | 0.5 | 5180 |
| Crystal form G of compound of Formula (III) | / | / | / | / | 903 | 0.75 | 3311 |
| Crystal form J of compound of Formula (IV) | / | / | / | / | 1083 | 0.5 | 3205 |

Note:
"/" means not tested; plasma clearance (Cl), apparent volume of distribution at steady state (Vdss), elimination half-life ($I_{1/2}$), area under the plasma concentration curve from time point 0 to the last quantifiable time point ($AUC_{0-last}$), peak concentration (Cmax), and peak time ($T_{max}$).

Conclusions: when administered intravenously, crystal form A of the compound of Formula (II) exhibits moderately low clearance, high volume of distribution, moderate half-life, and high level of drug exposure. When administered orally, crystal form A of the compound of Formula (II) shows rapid peak time, and high level of oral exposure, where the exposure level was higher than that of the crystal form G of the compound of Formula (III), and the crystal form J of the compound of Formula (III).

Test Example 3: In Vivo Pharmacodynamic Evaluation of the Compounds of the Present Invention SNU-16 cells in logarithmic growth phase were harvested, counted and resuspended in 50% PBS (pH 7.4, 0.01 M) and 50% Matrigel. The cell concentration was adjusted to $4\times10^7$ cells/mL, and the cells were then placed in an ice box. The cell suspension was aspirated with a 1 mL syringe and injected subcutaneously into the anterior right axilla of nude mice, at a dose of 200 μL/animal ($8\times10^6$ cells/animal) to establish a SNU-16 xenograft model. The animal status was observed periodically, and the tumor size was measured using an electronic vernier caliper. The data was entered into an Excel spreadsheet, and the tumor volume was calculated, to monitor the tumor growth. When the tumor volume reached 100-300 mm³, 35 tumor-bearing mice (with a tumor volume of 112-182 mm³) in good health status having similar tumor volume were selected and randomized into 5 groups (n=7). The average tumor volume in each group was about 150 mm³. After the test was started, the tumor size was measured twice a week, the tumor volume was calculated, and the body weight of the animal was weighed and recorded.

Analysis of tumor growth inhibition (TGI): The evolutionary growth potential of tumors was evaluated by the relationship between the tumor volume and time. The long axis (L) and short axis (W) of subcutaneous tumor were measured twice a week by a caliper, and the tumor volume (TV) was calculated by the formula (($L\times W^2$)/2). TGI was calculated from the difference between the median tumor volume of the mice in the solvent group and the median tumor volume of the mice in the drug group, and expressed as a percentage relative to the median tumor volume in the solvent control group.

TGI was calculated by the following formula:

% TGI=((median tumor volume (control)−median tumor volume (administration group))/median tumor volume (control group))×100%

The test data was calculated and statistically processed by SPSS19.0. Unless otherwise specified, the data were expressed as mean±standard error (Mean±SE), and the comparison between the two groups was analyzed by T-test. P<0.05 indicates that there is a significant difference. The solvent 30% PEG400 (containing 70% deionized water, v/v) alone was used as the negative control. The experimental results are shown in Table 22.

TABLE 22

Test results of in-vivo antitumor activity in mice

| | SNU-16 xenograft model | TGI % (the last dose is given on day 30) | p value |
|---|---|---|---|
| Crystal form A of compound of Formula (II) | 2.5 mg/kg BID | 72 | <0.005 |
| Crystal form A of compound of Formula (II) | 5.0 mg/kg BID | 86 | <0.005 |

Note:
BID: twice a day, TGI %: tumor growth inhibition rate

Conclusions: The crystal form A of the compound of Formula (II) exhibited excellent tumor inhibitory effect in the tumor model SNU-16.

What is claimed is:

1. A crystal form A of a compound of Formula (II), having an X-ray powder diffraction pattern with characteristic diffraction peaks at 2θ of 5.40°±0.20°, 11.99°±0.20°, and 14.77°±0.20°

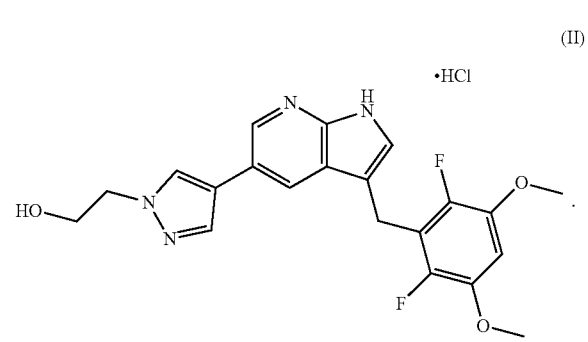 [SMILES: Cl ; COc1cc(OC)c(F)c(Cc2c[nH]c3ncc(-c4cnn(CCO)c4)cc23)c1F]

(II)

2. The crystal form A according to claim 1, having an X-ray powder diffraction pattern with characteristic diffraction peaks at 2θ of 5.40±0.20°, 10.77±0.20°, 11.99±0.20°, 14.77±0.20°, 21.55±0.20°, 23.25±0.20°, 24.14±0.20°, and 27.69±0.20°.

3. The crystal form A according to claim 2, having an X-ray powder diffraction pattern with characteristic diffraction peaks at 2θ of 5.402°, 8.949°, 10.766°, 11.989°, 13.186°, 14.766°, 16.090°, 16.779°, 19.721°, 21.554°, 23.251°, 23.685°, 24.138°, 25.224°, 27.690°, 28.670°, 29.287°, 31.378°, 33.941°, and 38.046°.

4. The crystal form A according to claim 1, having a differential scanning calorimetry profile with an endothermic peak starting at 220.0±3.0° C.

5. The crystal form A according to claim 1, having a thermogravimetric analysis curve showing a weight loss of 1.04% at 150.0° C.±3.0° C.

6. A crystal form G of a compound of Formula (III), having an X-ray powder diffraction pattern with characteristic diffraction peaks at 2θ of 6.86°±0.20°, 7.53°±0.20°, and 15.46°±0.20°,

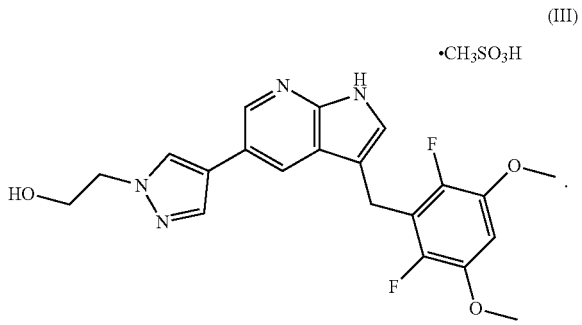 [SMILES: COc1cc(OC)c(F)c(Cc2c[nH]c3ncc(-c4cnn(CCO)c4)cc23)c1F ; "·CH3SO3H"]

(III)

7. The crystal form G according to claim 6, having an X-ray powder diffraction pattern with characteristic diffraction peaks at 2θ of 6.86±0.20°, 7.53±0.20°, 9.21±0.20°, 9.80±0.20°, 10.70±0.20°, 13.06±0.20°, 15.46±0.20°, and 20.53±0.20°.

8. The crystal form G according to claim 7, having an X-ray powder diffraction pattern with characteristic diffraction peaks at 2θ of 6.859°, 7.532°, 9.211°, 9.799°, 10.704°, 13.057°, 13.525°, 14.847°, 15.029°, 15.461°, 17.473°, 18.656°, 19.382°, 19.585°, 20.235°, 20.528°, 20.805°, 21.158°, 21.420°, 22.109°, 22.604°, 23.368°, 23.663°, 24.058°, 24.356°, 25.203°, 26.822°, 27.157°, 27.571°, 28.601°, 28.970°, 29.583°, 30.223°, 32.483°, 34.552°, 34.748°, and 35.268°.

9. The crystal form G according to claim 6, having a differential scanning calorimetry profile with an endothermic peak starting at 47.3±3.0° C., 86.8±3.0° C., and 145.2±3.0° C. respectively.

10. The crystal form G according to claim 6, having a thermogravimetric analysis curve showing a weight loss of 3.30% at 120.0° C.±3.0° C.

11. A crystal form J of a compound of Formula (IV), having an X-ray powder diffraction pattern with characteristic diffraction peaks at 2θ of 4.59°±0.20°, 7.02°±0.20°, and 18.05°±0.20°,

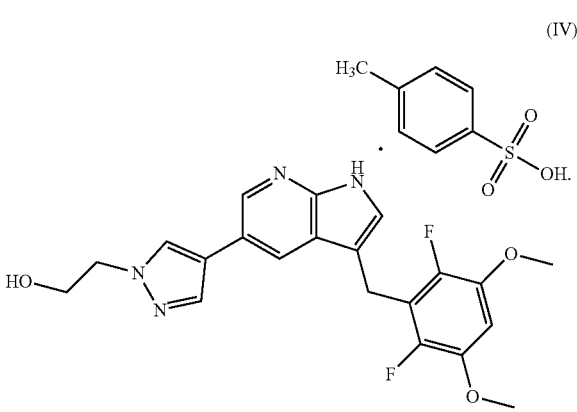 [SMILES: COc1cc(OC)c(F)c(Cc2c[nH]c3ncc(-c4cnn(CCO)c4)cc23)c1F ; Cc1ccc(S(=O)(=O)O)cc1]

(IV)

12. The crystal form J according to claim 11, having an X-ray powder diffraction pattern with characteristic diffraction peaks at 2θ of 4.59±0.20°, 7.02±0.20°, 10.13±0.20°, 14.06±020°, 18.05±0.20°, 19.82±0.20°, 22.56±020°, and 27.04±0.20°.

13. The crystal form J according to claim 12, having an X-ray powder diffraction pattern with characteristic diffraction peaks at 2θ of 4.592°, 6.094°, 7.018°, 9.383°, 10.132°, 11.535°, 12.241°, 14.059°, 18.046°, 19.819°, 21.435°, 22.561°, 23.764°, 24.117°, 26.489°, 27.035°, 28.732°, and 36.524°.

14. The crystal form J according to claim 11, having a thermogravimetric analysis curve showing a weight loss of 4.97% at 120.0° C.±3.0° C.

15. A crystal form N of a compound of Formula (I), having an X-ray powder diffraction pattern with characteristic diffraction peaks at 2θ of 12.64°±0.20°, 17.10°±0.20°, and 20.92°±0.20°

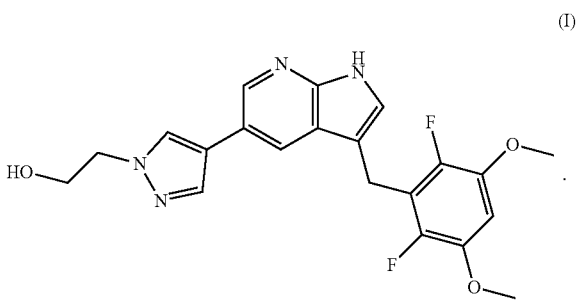 [SMILES: COc1cc(OC)c(F)c(Cc2c[nH]c3ncc(-c4cnn(CCO)c4)cc23)c1F]

(I)

16. The crystal form N according to claim 15, having an X-ray powder diffraction pattern with characteristic diffraction peaks at 2θ of 11.02±0.20°, 12.64±0.20°, 17.10±0.20°, 18.22±0.20°, 20.92±0.20°, 21.73±0.20°, 24.63±0.20°, and 26.65±0.20°.

17. The crystal form N according to claim 16, having an X-ray powder diffraction pattern with characteristic diffraction peaks at 2θ of 9.111°, 11.022°, 12.642°, 13.289°, 15.934°, 16.626°, 17.096°, 18.221°, 18.753°, 19.876°, 20.234°, 20.922°, 21.733°, 22.659°, 22.972°, 24.631°, 25.416°, 25.776°, 26.646°, 27.454°, 28.103°, 28.360°, 28.835°, 29.561°, 32.683°, 34.041°, 35.459°, 36.959°, and 37.886°.

18. A method of preparing a medicine for treating FGFR and c-Met related diseases, comprising:

mixing a crystal form G of a compound of Formula (III) or a crystal form J of a compound of Formula (IV), the crystal form A according to claim 1, or a crystal form N of a compound of Formula (I) with one or more pharmaceutically acceptable excipients;

wherein the crystal form G of the compound of Formula (III) has an X-ray powder diffraction pattern with characteristic diffraction peaks at 2θ of 6.86°±0.20°, 7.53°±0.20°, and 15.46°±0.20°, the crystal form J of the compound of Formula (IV) has an X-ray powder diffraction pattern with characteristic diffraction peaks at 2θ of 4.59°±0.20°, 7.02°±0.20°, and 18.05°±0.20°, the crystal form N of the compound of Formula (I) has an X-ray powder diffraction pattern with characteristic diffraction peaks at 2θ of 12.64°±0.20°, 17.10°±0.20°, and 20.92°±0.20°;

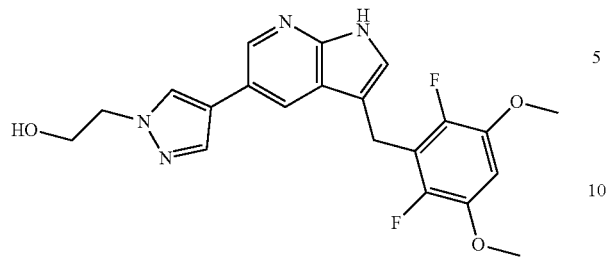
(I)
wherein the FGFR and c-Met related diseases comprise liver cancer, bladdercancer, lung cancer, breast cancer, endometrial cancer, glioma, prostate cancer, gastriccancer, non-small cell lung cancer, colorectal cancer, head and neck squamous cell carcinoma, hypopharyngeal cancer, and ovarian cancer.
* * * * *